(12) United States Patent
Du et al.

(10) Patent No.: US 11,332,440 B2
(45) Date of Patent: May 17, 2022

(54) 4-OXO-ALKYLATED TETRAMIC ACID COMPOUND, AND PREPARATION METHOD THEREOF

(71) Applicant: BEIJING JOEKAI BIOTECH. LLC, Beijing (CN)

(72) Inventors: Shuwen Du, Beijing (CN); Zuolei Xie, Beijing (CN)

(73) Assignee: BEIJING JOEKAI BIOTECH. LLC, Beijing (CN)

( * ) Notice: Subject to any disclaimer, the term of this patent is extended or adjusted under 35 U.S.C. 154(b) by 0 days.

(21) Appl. No.: 16/637,609

(22) PCT Filed: Jun. 20, 2018

(86) PCT No.: PCT/CN2018/091962
§ 371 (c)(1),
(2) Date: Feb. 7, 2020

(87) PCT Pub. No.: WO2019/029274
PCT Pub. Date: Feb. 14, 2019

(65) Prior Publication Data
US 2020/0181081 A1 Jun. 11, 2020

(30) Foreign Application Priority Data

Aug. 11, 2017 (CN) .......................... 201710684334.9

(51) Int. Cl.
| | | |
|---|---|---|
| A61P 25/00 | (2006.01) |
| A61P 25/28 | (2006.01) |
| A61P 25/18 | (2006.01) |
| C07D 409/12 | (2006.01) |
| C07D 401/12 | (2006.01) |
| C07D 207/38 | (2006.01) |

(52) U.S. Cl.
CPC ......... C07D 207/38 (2013.01); C07D 401/12 (2013.01); C07D 409/12 (2013.01)

(58) Field of Classification Search
CPC .. C07D 409/12; C07D 207/38; C07D 401/12; A61P 25/00; A61P 25/28; A61P 25/18
See application file for complete search history.

(56) References Cited

U.S. PATENT DOCUMENTS

| 5,286,650 A | 2/1994 | Banziger et al. |
| 2010/0261608 A1 | 10/2010 | Fischer et al. |

FOREIGN PATENT DOCUMENTS

| CN | 1914172 A | 2/2007 |
| CN | 101679245 A | 3/2010 |
| CN | 101838260 A | 9/2010 |
| CN | 103459370 A | 12/2013 |
| CN | 104411683 A | 3/2015 |
| CN | 104995176 A | 10/2015 |
| CN | 107056672 A | 8/2017 |
| CN | 107353239 A | 11/2017 |
| CN | 107468690 A | 12/2017 |
| EP | 3643311 A1 | 4/2020 |
| WO | 2005058857 A1 | 6/2005 |
| WO | 2010020055 A1 | 2/2010 |
| WO | 2014006629 A1 | 1/2014 |
| WO | 2019029273 A1 | 2/2019 |
| WO | 2019029274 A1 | 2/2019 |

OTHER PUBLICATIONS

RN2160558-76-7, registry database compound, entry date 2017.*
International Search Report issued in corresponding International Application No. PCT/CN2018/091962; dated Aug. 15, 2018; China National Intellectual Administration, Beijing, China, 10 pgs.
International Search Report issued in International Application No. PCT/CN2018/091961, dated Sep. 30, 2018; China National Intellectual Administration, Beijing, China, 6 pgs.
Examination Report No. 1 issued in Australian Patent Application No. 2018314471; dated May 12, 2020; 6 pgs.
Examination Report No. 2 issued in Australian Patent Application No. 2018314471; dated Feb. 4, 2021; 9 pgs.
Supplementary European Search Report issued in European Patent Application No. 18843726; dated Feb. 2, 2021; 2 pgs.
Supplementary European Search Report issued in European Patent Application No. 18844790; dated Mar. 3, 2021; 2 pgs.
First Office Action issued in Chinese Patent Application No. 201710684334.9; dated Mar. 8, 2019; 10 pgs.
Search Report issued in Chinese Patent Application No. 201710684334.9; dated Feb. 25, 2019; 3 pgs.
First Office Action issued in Chinese Patent Application No. 201710684789.0; dated Nov. 19, 2019; 10 pgs.

(Continued)

*Primary Examiner* — Sun Jae Yoo

(74) *Attorney, Agent, or Firm* — Hauptman Ham, LLP

(57) ABSTRACT

The present invention relates to a new compound and a preparation method thereof. The general structural formula of the compound is shown in Formula I. Animal experiments show that the compound has the effect of saving the memory of animal models. It is of high safety, has no mutagenicity, can remain in blood for several hours after oral or intravenous injection, and can enter the brain. The compound can be used for preparing a medicament for treating Alzheimer's disease.

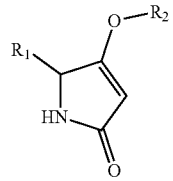

Formula I

6 Claims, 4 Drawing Sheets

(56) References Cited

OTHER PUBLICATIONS

Schobert et al.; Synthesis and reactions of polymer-bound Ph3P=C=C=O: a quick route to tenuazonic acid and other optically pure 5-substituted tetramates; Org Biomol. Chem., 2004, 2, 3524-3529.

* cited by examiner

4-OXO-ALKYLATED TETRAMIC ACID COMPOUND, AND PREPARATION METHOD THEREOF

RELATED APPLICATIONS

The present application is a National Phase of International Application Number PCT/CN2018/091962, filed Jun. 20, 2018, which claims priority to Chinese Application Number 201710684334.9, filed Aug. 11, 2017.

FIELD OF THE INVENTION

The present invention relates to the field of pharmaceuticals, and in particular to 4-oxo-alkylated tetramic acid compounds, and preparation methods.

BACKGROUND OF THE INVENTION

Learning and memory abilities are very important in daily life, and impairment of learning and memory abilities caused by various diseases has brought great damage to patients. Common diseases causing learning and memory impairment include Parkinson's disease, Huntington's disease, various types of dementia, schizophrenia, and autism among others. Alzheimer's disease is a common neurodegenerative disease, accompanied by memory loss, neuronal death, and other symptoms, with senile plaques and nerve fiber tangles as the main clinical signs. At present, therapeutic means is relatively insufficient for the disease. More than a decade ago, the FDA approved altogether five therapeutic compounds of two types, including cholinesterase inhibitors and NMDA receptor antagonists, which, however, can only temporarily relieve the symptoms of the disease, instead of preventing the course thereof. Therefore, both the scientific community and the business community are actively engaged in understanding the mechanism of the disease and the development of related medicaments. In order to understand the disease and develop medicaments, many animal models with human pathogenic genes have been developed and used in the development of therapeutic medicaments. Currently, the most popular hypothesis is the amyloid hypothesis, i.e., the Abeta protein is the main cause of neuropathological changes, and several transgenic models have been constructed accordingly. Based on this hypothesis, pharmaceutical companies have developed many vaccines targeting the Abeta protein and phosphorylation inhibitors of various enzymes in the process of forming the protein. However, these efforts have ended ineffective so far.

We think it is be too late to reduce the amount of the protein after the onset of the disease in patients. Development of therapeutic medicaments should start from reducing the toxicity of the protein. Therefore, starting from improving the cognitive function of animal models, the present invention searches for medicaments for treating Alzheimer's disease, and finds out a series of new compounds that have the features of good therapeutic effects, good pharmacological characteristics, high safety, etc. These compounds have the potential to treat not only Alzheimer's disease, but also Parkinson's disease, Huntington's disease, vascular dementia, schizophrenia, autism, and other diseases.

SUMMARY OF THE INVENTION

The objective of the present invention is to provide a 4-oxo-alkylated tetramic acid compound and a method of preparing the same.

The 4-oxo-alkylated tetramic acid compound provided by the present invention has the structural formula as shown in Formula I:

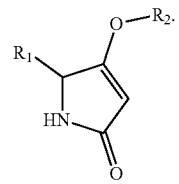

Formula I

In Formula I, $R_1$ can be selected from

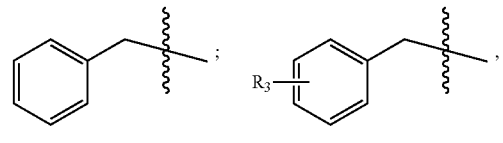

wherein $R_3$ can be a C1-C6 alkoxy group, particularly a methoxy group;

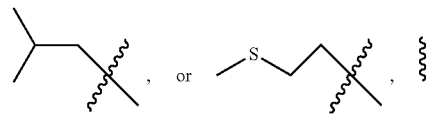

representing a connecting end.

$R_2$ can be selected from

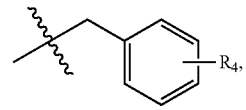

wherein $R_4$ can be a 2-, 3-, or 4-position monosubstituted halogen, particularly 2-, 3-, or 4-position monosubstituted fluorine, 2-, 3-, or 4-position monosubstituted C1-C6 alkyl or alkoxy group, particularly 2- or 4-position substituted methoxy group or 4-position substituted methoxy group, ester group, particularly 4-position substituted —OAc, 4-position substituted

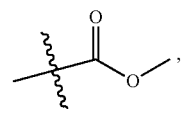 [SMILES: *C(=O)OC]

4-position substituted —CN, 4-position substituted —NO$_2$, disubstituted alkoxy group, particularly 2-,3-position disubstituted methoxy group or 2-,5-position disubstituted methoxy group;

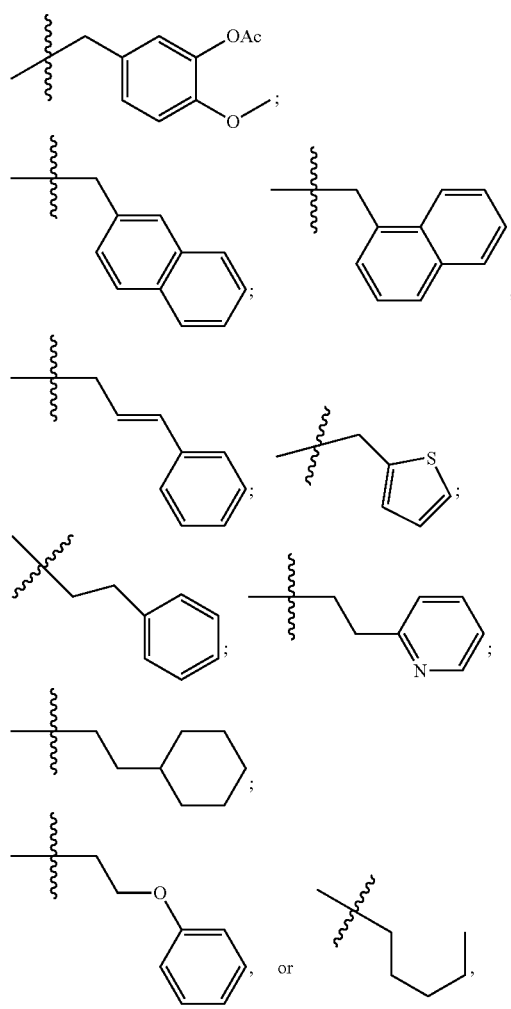
ξ representing a connecting end.
Salts of the compounds shown in Formula I also fall within to the protection scope of the present invention.
Particularly, the 4-oxo-alkylated tetramic acid compound shown in Formula I of the present invention is one of the following compounds:
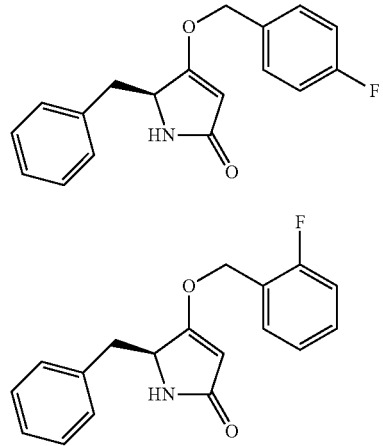
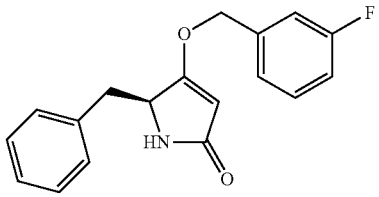
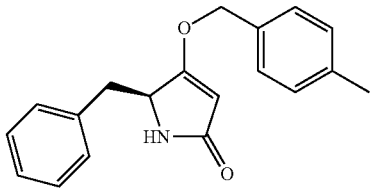
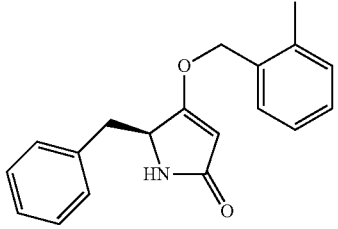
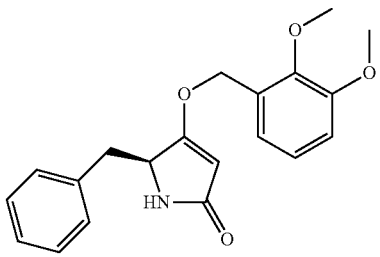
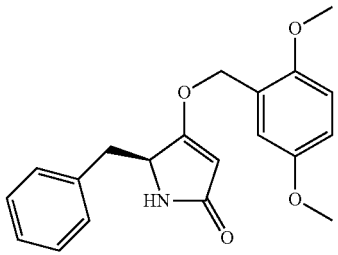
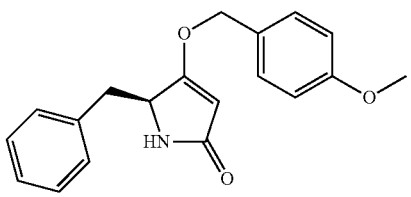
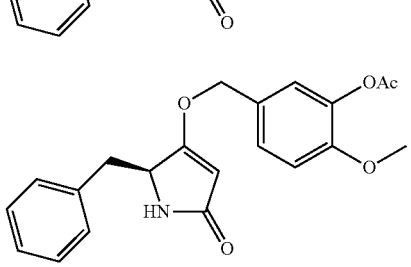

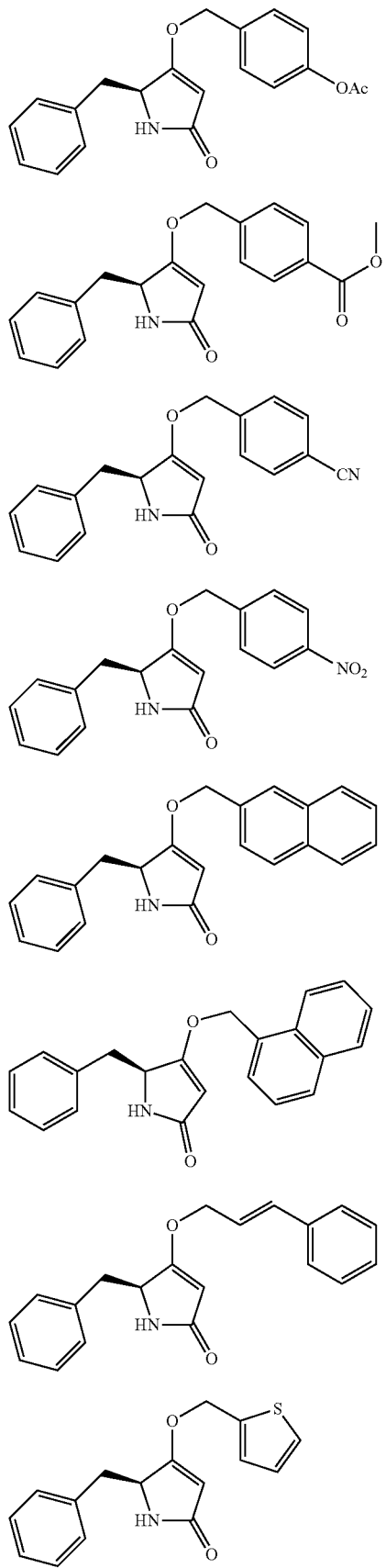
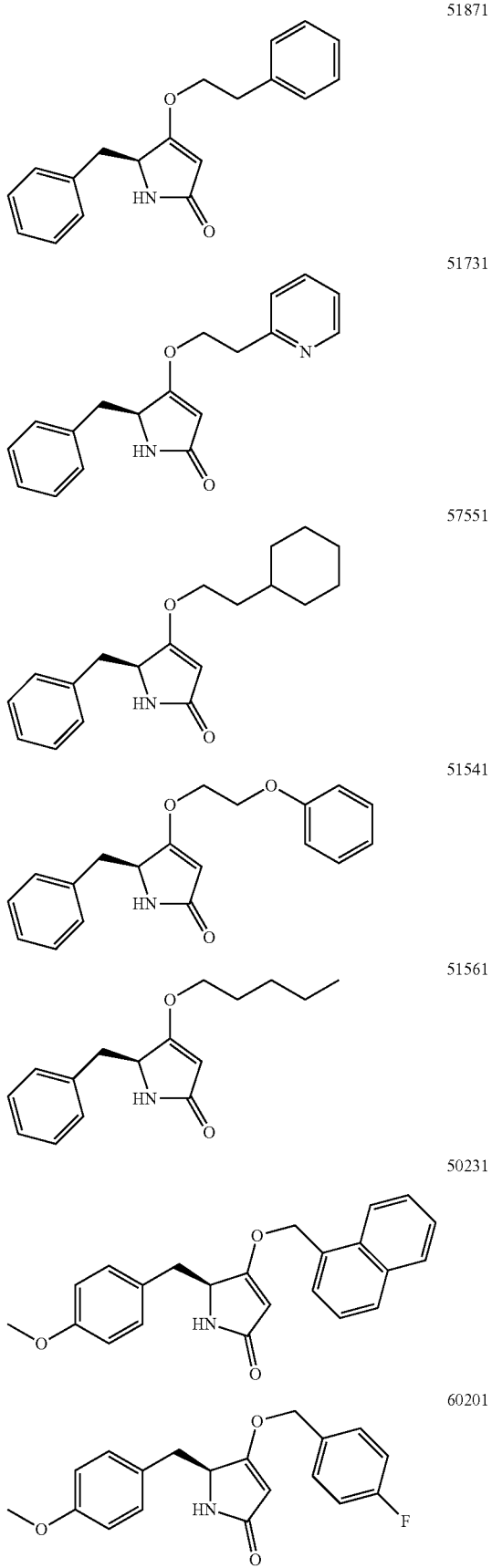

-continued

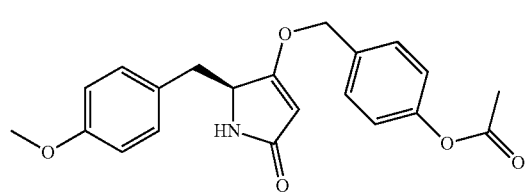
60111

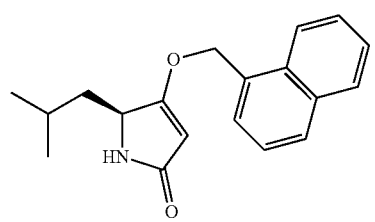
60241

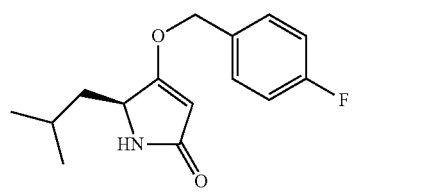
60211

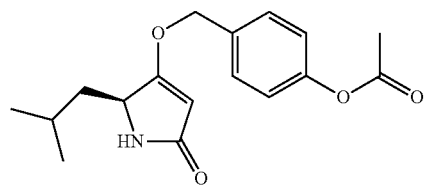
60121

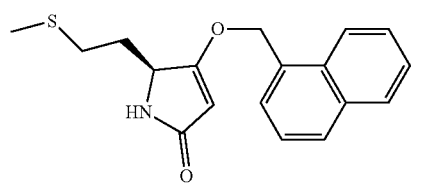
60251

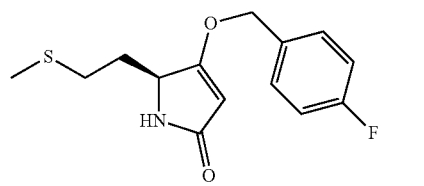
60221

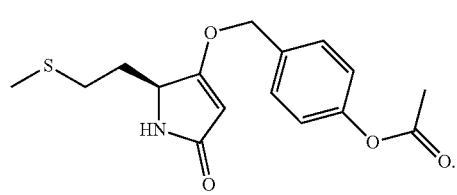
60131

The 4-oxo-alkylated tetramic acid compound as shown in Formula I above is prepared by a method comprising the following steps:

1) reacting a compound shown in Formula II with a compound shown in Formula III to obtain a compound shown in Formula IV,

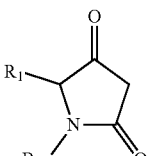

Formula II

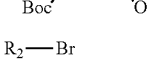

Formula III

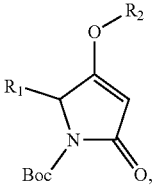

Formula IV wherein in above Formula II and Formula IV, $R_1$ has the same definition as in Formula I, and Boc represents tert-butoxycarbonyl group; and in above Formula III and Formula IV, $R_2$ has the same definition as in Formula I; and 2) removing the compound shown in Formula IV from Boc protection to obtain the compound shown in Formula I.

In step 1) of the above method, the molar ratio of the compound shown in Formula II to the compound shown in Formula III can be 1:1-10.

The reaction can be carried out under alkaline conditions, and the alkali can be potassium carbonate.

The reaction temperature can be 0-100 degrees C. and the reaction time can be 0.1-24 hours.

The reaction can be carried out in an organic solvent, which can in particular be acetonitrile.

In step 2) of the above method, the removal of Boc protection can be carried out under the action of trifluoroacetic acid.

The molar ratio of the compound shown in Formula IV to trifluoroacetic acid can be 1:1-20, particularly can be 1:3.

The reaction temperature for removal of Boc protection can be −10 to 30 degrees C., in particular room temperature, and the reaction time thereof can be 0.5-24 hours, in particular can be 5 hours.

The removal of Boc protection is carried out in an organic solvent, and in particular can be dichloromethane.

Use of the 4-oxo-alkylated tetramic acid compound shown in above Formula I or the salt thereof in the preparation of a medicament for treating Alzheimer's disease, vascular dementia, and other dementia diseases with impaired memory also falls within the protection scope of the present invention.

The present invention also provides a medicament for treating Alzheimer's disease, vascular dementia, and other dementia diseases with impaired memory, comprising the 4-oxo-alkylated tetramic acid compound shown in Formula I or the salt thereof.

Animal experiments show that the compound of the present invention has the effect of saving the memory of animal models, and is of high safety, has no mutagenicity, is capable of staying in blood for several hours after oral or intravenous injection, and can enter the brain.

DETAILED DESCRIPTION OF EXAMPLES

Figure 1:
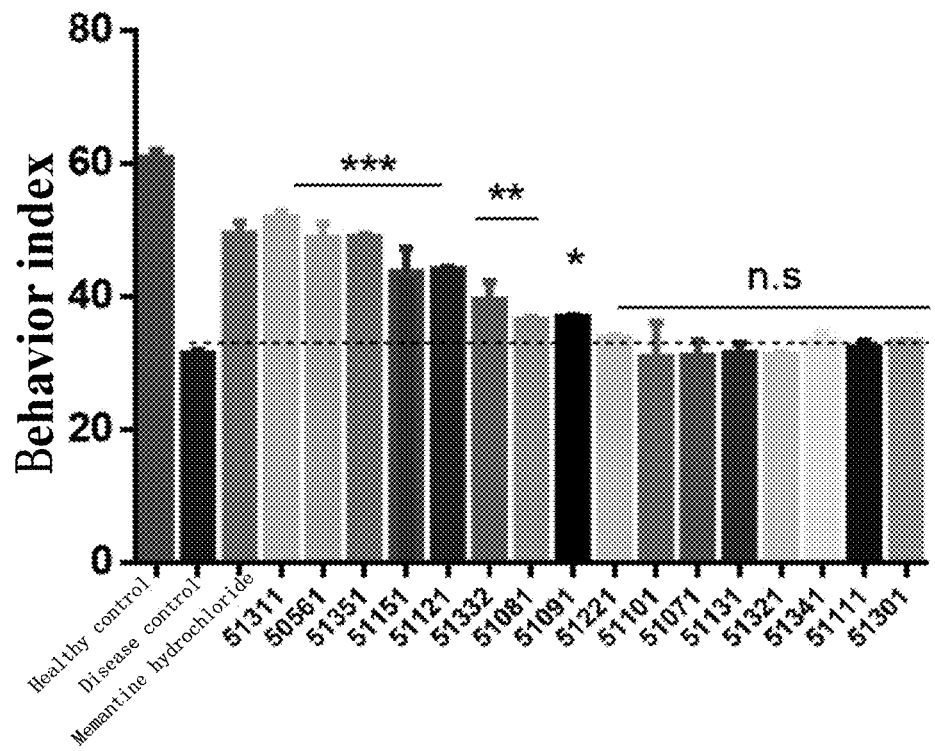
FIG. 1 shows the effect of compounds 51311, 50561, 51351, 51151, 51121, 51332, 51081, 51091, 51221, 51101, 51071, 51131, 51321, 51341, 51111, and 51301 on memory improvement of Drosophilae with Alzheimer's disease.

The experimental methods in the following examples, unless otherwise specified, are conventional methods.

Example 1 Preparation of Compound

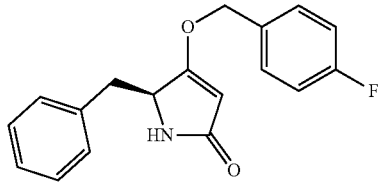 [SMILES: O=C1C=C(OCc2ccc(F)cc2)[C@H](Cc2ccccc2)N1]

50561

1.1 Preparation of

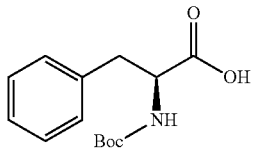 [SMILES: CC(C)(C)OC(=O)N[C@@H](Cc1ccccc1)C(=O)O]

Intermediate 1

L-phenylalanine (20 g, 121.07 mmol) was dissolved into 500 mL of a mixture solution of tetrahydrofuran and water (v/v 1:1), followed by stirring for 10 minutes in ice bath. Sodium hydroxide (10.7 g, 266.4 mmol) and di-tert-butyl dicarbonate (29.1 g, 133.2 mmol) were added in batches, followed by 10 hours of stirring at room temperature. TLC monitoring showed that the reaction was completed. Tetrahydrofuran was removed by reduced pressure evaporation, and 500 mL of dichloromethane was added. 2N hydrochloric acid solution was added dropwise under stirring until the water layer had a pH value of about 5. An organic layer was separated, washed once with 200 mL of saturated brine, and dried with anhydrous magnesium sulfate. Filtration was performed, and the solvent was removed by reduced pressure evaporation to obtain a crude product, with a yield of 99%. A next reaction could be carried out without further purification.

1.2 Preparation of

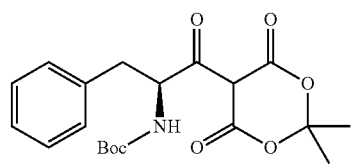 [SMILES: CC(C)(C)OC(=O)N[C@@H](Cc1ccccc1)C(=O)C1C(=O)OC(C)(C)OC1=O]

Intermediate 2

Intermediate 1 (25 g, 94.2 mmol) was dissolved into 500 mL of anhydrous dichloromethane. Meldrum's acid (14.9 g, 103.7 mmol) and 4-dimethylaminopyridine (17.3 g, 141.3 mmol) were added in turn, followed by stirring under ice bath for 10 minutes. A solution of dicyclohexylcarbodiimide (21.4 g, 103.7 mmol) in dichloromethane (100 mL) was added dropwise. After that, the reaction liquid continued to be stirred for 10 hours in ice bath, and the reaction was completed as monitored by TLC. Filtration was performed. The filtrate was washed six times with 5% potassium bisulfate aqueous solutions, 200 mL each time, washed once with saturated brine, and dried with anhydrous sodium sulfate. And the solvent was removed by reduced pressure evaporation to obtain a yellowish solid. 500 mL of petroleum ether was added, followed by stirring and filtration to obtain a target product, i.e., a white solid (30 g, yield: 77%). A next reaction could be carried out without further purification.

1.3 Preparation of

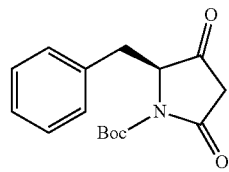 [SMILES: CC(C)(C)OC(=O)N1C(=O)CC(=O)[C@@H]1Cc1ccccc1]

Intermediate 3

Intermediate 2 (25 g, 63.9 mmol) was dissolved into 400 mL of ethyl acetate, followed by reflux reaction for 5 hours. After cooling down to room temperature, ethyl acetate was evaporated under reduced pressure to obtain a while solid, i.e., the target product (17.6 g, 95%). The product did not need further purification.

1.4 Preparation of

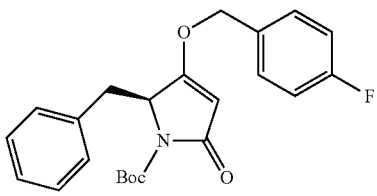 [SMILES: CC(C)(C)OC(=O)N1C(=O)C=C(OCc2ccc(F)cc2)[C@@H]1Cc1ccccc1]

01311, Intermediate 15

Intermediate 3 (289 mg, 1.0 mmol) was dissolved into 5 mL of acetonitrile. $K_2CO_3$ (207 mg, 1.5 mmol) and 4-fluorobenzyl bromide (227 mg, 1.2 mmol) were added in turn at room temperature, followed by reflux reaction for 5 hours. After cooling to room temperature, filtration was performed to remove solids. The filtrate was dried by evaporation. Column chromatography purification was performed to obtain intermediate 15, i.e., as a colorless oily substance (158 mg, yield: 40%). Molecular weight: 397.45. $^1$H NMR (400 MHz, $CDCl_3$) δ 7.34 (dd, J=8.2, 5.4 Hz, 2H), 7.19 (m, 3H), 7.10 (t, J=8.5 Hz, 2H), 6.98 (m, 2H), 4.91 (s, 1H), 4.84 (m, 2H), 4.71 (dd, J=5.3, 3.0 Hz, 1H), 3.43 (dd, J=14.0, 5.2 Hz, 1H), 3.14 (dd, J=14.0, 2.8 Hz, 1H), 1.59 (s, 9H). $^{13}$C NMR (100 MHz, $CDCl_3$) δ 174.79, 168.75, 163.06 (d, J=248.3 Hz), 149.47, 134.24, 130.21 (d, J=8.4 Hz), 130.05 (d, J=3.3 Hz), 129.59, 128.35, 127.11, 115.93 (d, J=21.7 Hz), 96.18, 82.78, 72.65, 60.38, 35.55, 28.30. $^{19}$F NMR (376 MHz, $CDCl_3$) δ -112.20.

1.5 Preparation of Compound

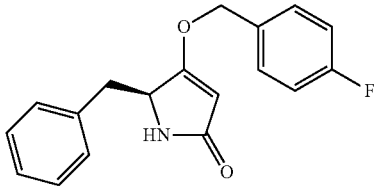 [SMILES: O=C1C=C(OCc2ccc(F)cc2)[C@H](Cc2ccccc2)N1]

50561

Intermediate 15 (397 mg, 1.0 mmol) was dissolved into 10 mL of dichloromethane. Trifluoroacetic acid (223 μL, 3.0 mmol) was added under ice bath. The reaction liquid was reacted for 5 hours under stirring at room temperature. After the reaction was completed, 90 mL of dichloromethane was added to dilute the reaction solution. Washing was performed with 10% $NaHCO_3$ solution once, and then with saturated brine once. Drying with anhydrous sodium sulfate, and filtration were performed. The solvent was removed by evaporation. Column chromatography was performed for separation and purification to obtain 360 mg of the white solid of Example 1 with a yield of 82%. Molecular weight: 297.33. $^1$H NMR (400 MHz, $CDCl_3$) δ 7.37 (dd, J=8.4, 5.3 Hz, 2H), 7.27 (m, 3H), 7.18 (m, 2H), 7.11 (t, J=8.5 Hz, 2H), 5.77 (s, 1H), 5.06 (s, 1H), 4.95 (m, 2H), 4.27 (dd, J=9.2, 3.6 Hz, 1H), 3.21 (dd, J=13.7, 3.7 Hz, 1H), 2.67 (dd, J=13.7, 9.0 Hz, 1H). $^{13}$C NMR (100 MHz, $CDCl_3$) δ 175.94, 173.55, 163.04 (d, J=247.8 Hz), 136.55, 130.64 (d, J=3.5 Hz), 130.06 (d, J=8.4 Hz), 129.27, 128.79, 127.17, 115.91 (d, J=21.7 Hz), 95.23, 72.60, 58.86, 38.77. $^{19}$F NMR (376 MHz, $CDCl_3$) δ -112.58.

Example 2 Preparation of Compound

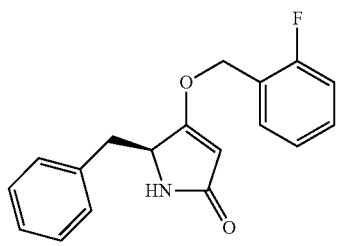 [SMILES: O=C1C=C(OCc2ccccc2F)[C@H](Cc2ccccc2)N1]

51121

2.1 Preparation of

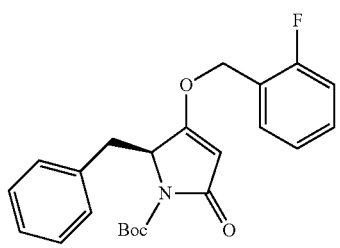 [SMILES: CC(C)(C)OC(=O)N1C(=O)C=C(OCc2ccccc2F)[C@@H]1Cc1ccccc1]

50951, Intermediate 16

The same synthesis method as for intermediate 15 was used, but 2-fluorobenzyl bromide was used to replace 4-fluorobenzyl bromide to prepare intermediate 16, as a colorless oily substance (259 mg, yield: 65%). Molecular weight: 397.45. $^1$H NMR (400 MHz, $CDCl_3$) δ 7.38 (m, 2H), 7.18 (m, 5H), 6.99 (m, 2H), 4.95 (m, 3H), 4.70 (s, 1H), 3.43 (dd, J=13.9, 4.7 Hz, 1H), 3.13 (d, J=13.9 Hz, 1H), 1.59 (s, 9H). $^{13}$C NMR (100 MHz, $CDCl_3$) δ 174.67, 168.62, 160.93 (d, J=249.0 Hz), 149.46, 134.13, 131.27 (d, J=8.3 Hz), 130.75 (d, J=3.2 Hz), 129.62, 129.62, 127.03, 124.54 (d, J=3.7 HZ), 121.43 (d, J=14.4 Hz), 115.83 (d, J=21.1 Hz), 96.09, 82.65, 67.12 (d, J=4.2 Hz), 60.34, 35.44, 28.27. $^{19}$F NMR (376 MHz, $CDCl_3$) δ -117.44.

2.2 Preparation of Compound

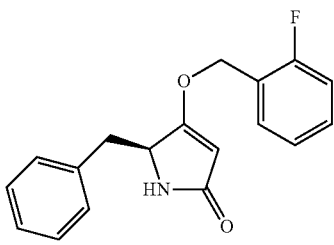 [SMILES: O=C1C=C(OCc2ccccc2F)[C@H](Cc2ccccc2)N1]

51121

Intermediate 16 (402 mg, 1.01 mmol) was used as raw material and the same synthesis method as in Example 1 was adopted to prepare 258 mg of the white solid of Example 2 with a yield of 86%. Molecular weight: 297.33. $^1$H NMR (400 MHz, CDCl$_3$) δ 7.39 (m, 1H), 7.19 (m, 7H), 6.39 (brs, 1H), 5.08 (s, 1H), 5.02 (m, 2H), 4.28 (dd, J=8.4, 3.8 Hz, 1H), 3.16 (dd, J=13.7, 4.1 Hz, 1H), 2.72 (dd, J=13.6, 8.1 Hz, 1H). $^{13}$C NMR (100 MHz, CDCl$_3$) δ 175.72, 173.78, 160.85 (d, J=248.7 Hz), 136.26, 130.91 (d, J=8.3 Hz), 130.42 (d, J=3.5 Hz), 129.34, 128.54, 126.95, 124.45 (d, J=3.7 Hz), 122.00 (d, J=14.4 Hz), 115.74 (d, J=21.2 Hz), 95.20, 66.95 (d, J=4.1 Hz), 58.68, 38.35. $^{19}$F NMR (376 MHz, CDCl$_3$) δ -117.70.

Example 3 Preparation of Compound

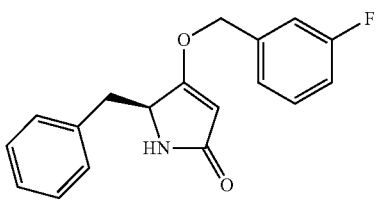 [SMILES: O=C1C=C(OCc2cccc(F)c2)[C@H](Cc2ccccc2)N1]

51131

3.1 Preparation of

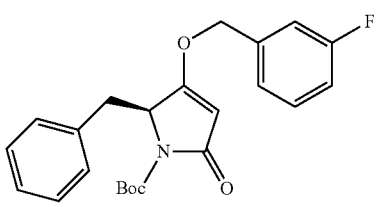 [SMILES: CC(C)(C)OC(=O)N1C(=O)C=C(OCc2cccc(F)c2)[C@@H]1Cc1ccccc1]

50941, Intermediate 17

The same synthesis method as for intermediate 15 was adopted, but 3-fluorobenzyl bromide was used instead of 4-fluorobenzyl bromide to prepare intermediate 17, a colorless oily substance (158 mg, yield: 40%). Molecular weight: 397.45. $^1$H NMR (400 MHz, CDCl$_3$) δ 7.37 (m, 1H), 7.21 (m, 3H), 7.04 (m, 5H), 4.91 (s, 1H), 4.88 (m, 2H), 4.74 (m, 1H), 3.43 (dd, J=14.0, 5.4 Hz, 1H), 3.18 (dd, J=14.1, 3.0 Hz, 1H), 1.60 (s, 9H). $^{13}$C NMR (100 MHz, CDCl$_3$) δ 174.76, 168.59, 163.00 (d, J=247.3 Hz), 149.50, 136.62 (d, J=7.5 Hz), 134.31, 130.58 (d, J=8.3 Hz), 129.61, 128.41, 127.17, 123.40 (d, J=3.0 Hz), 115.97 (d, J=21.0 Hz), 114.84 (d, J=22.2 Hz), 96.40, 82.83, 72.42 (d, J=2.0 Hz), 60.42, 35.69, 28.33. $^{19}$F NMR (376 MHz, CDCl$_3$) δ -111.95.

3.2 Preparation of Compound

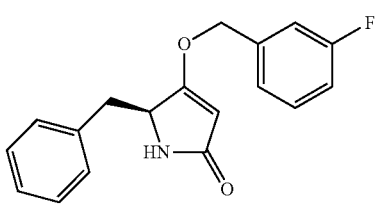 [SMILES: O=C1C=C(OCc2cccc(F)c2)[C@H](Cc2ccccc2)N1]

51131

Intermediate 17 (308 mg, 0.77 mmol) was used as raw material and the same synthesis method as in Example 1 was adopted to prepare 229 mg of the white solid of Example 3 with a yield of 100%. Molecular weight: 297.33. $^1$H NMR (400 MHz, CDCl$_3$) δ 7.20 (m, 9H), 5.76 (s, 1H), 5.05 (s, 1H), 4.98 (m, 2H), 4.30 (dd, J=9.2, 3.7 Hz, 1H), 3.23 (dd, J=13.7, 3.7 Hz, 1H), 2.69 (dd, J=13.6, 9.0 Hz, 1H). $^{13}$C NMR (100 MHz, CDCl$_3$) δ 175.82, 173.41, 163.06 (d, J=246.9 Hz), 137.24 (d, J=7.5 Hz), 136.52, 130.54 (d, J=8.2 Hz), 129.28, 128.83, 127.22, 123.31 (d, J=3.0 Hz), 115.83 (d, J=21.1 Hz), 114.74 (d, J=22.2 Hz), 95.45, 72.36 (d, J=2.0 Hz), 58.84, 38.80. $^{19}$F NMR (376 MHz, CDCl$_3$) δ -112.12.

Example 4 Preparation of Compound

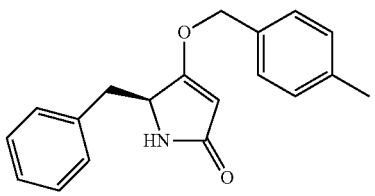 [SMILES: Cc1ccc(COC2=CC(=O)N[C@H]2Cc2ccccc2)cc1]

51091

4.1 Preparation of

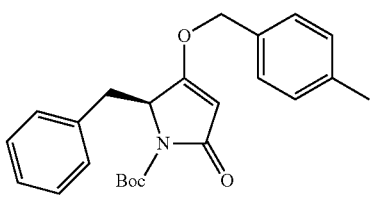 [SMILES: Cc1ccc(COC2=CC(=O)N(C(=O)OC(C)(C)C)[C@H]2Cc2ccccc2)cc1]

51031, Intermediate 18

The same synthesis method as for intermediate 15 was adopted, but 4-methyl benzyl bromide was used instead of 4-fluorobenzyl bromide to prepare intermediate 18, as a colorless oily substance (176 mg, yield: 45%). Molecular weight: 393.48. $^1$H NMR (400 MHz, CDCl$_3$) δ 7.22 (m, 7H), 6.98 (m, 2H), 4.91 (s, 1H), 4.86 (m, 2H), 4.70 (dd, J=5.2, 3.1 Hz, 1H), 3.44 (dd, J=14.0, 5.2 Hz, 1H), 3.13 (dd, J=14.0, 3.0 Hz, 1H), 2.39 (s, 3H), 1.59 (s, 9H). $^{13}$C NMR (100 MHz, CDCl$_3$) δ 175.00, 168.91, 149.61, 139.15, 134.33, 131.24, 129.72, 129.64, 128.44, 128.36, 127.12, 96.15, 82.72, 73.46, 60.47, 35.52, 28.37, 21.38.

4.2 Preparation of Compound

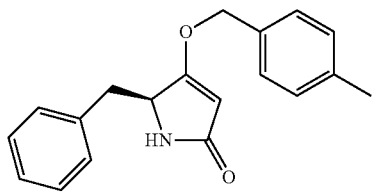 [SMILES: Cc1ccc(COC2=CC(=O)N[C@H]2Cc2ccccc2)cc1]

51091

Intermediate 18 (176 mg, 0.45 mmol) was used as raw material, and the same synthesis method as in Example 1 was used to prepare 96 mg of the white solid of Example 4 with a yield of 73%. Molecular weight: 293.37. $^1$H NMR (400 MHz, CDCl$_3$) δ 7.24 (m, 9H), 5.50 (s, 1H), 5.06 (s, 1H), 4.95 (m, 2H), 4.25 (dd, J=9.5, 3.4 Hz, 1H), 3.23 (dd, J=13.6, 3.5 Hz, 1H), 2.63 (dd, J=13.6, 9.4 Hz, 1H), 2.39 (s, 3H). $^{13}$C NMR (100 MHz, CDCl$_3$) δ 176.20, 173.64, 138.95, 136.76, 131.79, 129.60, 129.27, 128.84, 128.29, 127.17, 95.03, 73.37, 58.95, 38.88, 21.39.

Example 5 Preparation of Compound

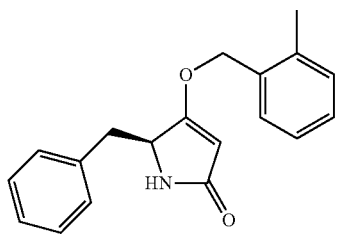 [SMILES: Cc1ccccc1COC1=CC(=O)N[C@H]1Cc1ccccc1]

51101

5.1 Preparation of

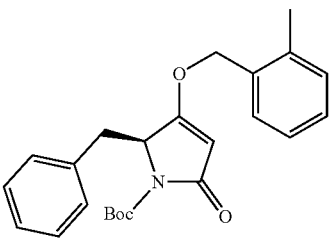 [SMILES: Cc1ccccc1COC1=CC(=O)N(C(=O)OC(C)(C)C)[C@H]1Cc1ccccc1]

51041, Intermediate 19

The same synthesis method as for intermediate 15 was used, but 2-methyl benzyl bromide was used instead of 4-fluorobenzyl bromide to prepare intermediate 19, a colorless oily substance (205 mg, yield: 52%). Molecular weight: 393.48. $^1$H NMR (400 MHz, CDCl$_3$) δ 7.23 (m, 7H), 6.97 (m, 2H), 4.97 (s, 1H), 4.92 (m, 2H), 4.72 (m, 1H), 3.45 (dd, J=14.0, 5.1 Hz, 1H), 3.13 (dd, J=14.0, 2.5 Hz, 1H), 2.38 (s, 3H), 1.60 (s, 9H). $^{13}$C NMR (100 MHz, CDCl$_3$) δ 175.02, 168.84, 149.61, 137.07, 134.29, 132.32, 130.82, 129.70, 129.45, 128.37, 127.13, 126.41, 96.09, 82.75, 71.88, 60.45, 35.54, 28.37, 19.05.

5.2 Preparation of Compound

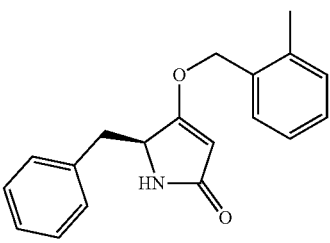 [SMILES: Cc1ccccc1COC1=CC(=O)N[C@H]1Cc1ccccc1]

51101

Intermediate 19 (205 mg, 0.52 mmol) was used as raw material, and the same synthesis method as in Example 1 was adopted to prepare 114 mg of the white solid of Example 5, with a yield of 75%. Molecular weight: 293.37. $^1$H NMR (400 MHz, CDCl$_3$) δ 7.27 (m, 9H), 5.78 (s, 1H), 5.11 (s, 1H), 4.99 (m, 2H), 4.26 (dd, J=9.4, 3.4 Hz, 1H), 3.21 (dd, J=13.6, 3.5 Hz, 1H), 2.64 (dd, J=13.6, 9.3 Hz, 1H), 2.38 (s, 3H). $^{13}$C NMR (100 MHz, CDCl$_3$) δ 176.17, 173.67, 137.19, 136.66, 132.75, 130.76, 129.40, 129.31, 129.26, 128.77, 127.12, 126.31, 94.91, 71.92, 58.93, 38.80, 19.00.

Example 6 Preparation of Compound

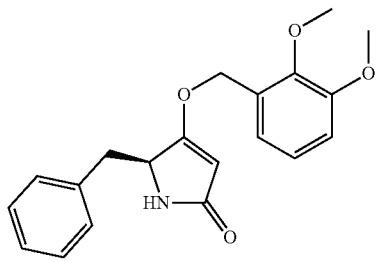 [SMILES: COc1cccc(COC2=CC(=O)N[C@H]2Cc2ccccc2)c1OC]

51071

6.1 Preparation of

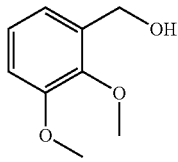

2,3-dimethoxybenzaldehyde (1.66 g, 10 mmol) was dissolved into 50 mL of anhydrous tetrahydrofuran, followed by stirring under ice bath for 10 minutes. Lithium-aluminium tetrahydride (0.19 g, 5 mmol) was added in batches, followed by reaction under stirring in ice bath for 30 minutes. Saturated ammonium chloride aqueous solution was added to quench the reaction. Extraction was performed three times with ethyl acetate (100 mL×3). Organic layers were combined, and dried by anhydrous sodium sulfate. After filtration, the solvent was removed by reduced pressure evaporation to obtain a target product (1.6 g, yield: 95%). A next step reaction could be performed without further purification.

6.2 Preparation of

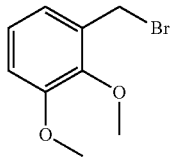

2,3-dimethoxybenzyl alcohol (1.6 g, 9.5 mmol) was dissolved into 50 mL of anhydrous dichloromethane, followed by stirring in ice bath for 10 minutes. Phosphorus tribromide (0.87 g, 3.2 mmol) was added dropwise slowly. After that reaction continued under ice bath for 1 hour. After 200 mL of dichloromethane was added to dilute the reaction solution, water washing (50 mL×3), saturated brine washing (100 mL×1), drying with anhydrous sodium sulfate, and filtration were performed. And the solvent was removed by reduced pressure evaporation to produce a crude product, which was purified by column chromatography to obtain 2,3-dimethoxybenzyl bromide (2.1 g, yield: 96%). $^1$H NMR (400 MHz, CDCl$_3$) δ 7.03 (m, 1H), 6.96 (dd, J=7.8, 1.7 Hz, 1H), 6.88 (dd, J=8.0, 1.6 Hz, 1H), 4.57 (s, 2H), 3.97 (s, 3H), 3.87 (s, 3.87 (s, 3H). $^{13}$C NMR (100 MHz, CDCl$_3$) δ 152.89, 147.55, 131.95, 124.22, 122.61, 113.13, 60.90, 55.91, 28.24.

6.3 Preparation of

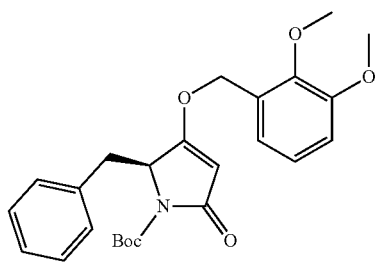 [SMILES: COc1cccc(COC2=CC(=O)N(C(=O)OC(C)(C)C)[C@H]2Cc2ccccc2)c1OC]

51011, Intermediate 20

The same synthesis method as for intermediate 15 was adopted, but 2,3-dimethoxybenzyl bromide instead of 4-fluorobenzyl bromide was used to prepare intermediate 20, a colorless oily substance (191 mg, yield: 43%). Molecular weight: 439.51. $^1$H NMR (400 MHz, CDCl$_3$) δ 7.05 (m, 8H), 4.97 (s, 1H), 4.94 (m, 2H), 4.69 (dd, J=4.6, 2.8 Hz, 1H), 3.88 (s, 6H), 3.43 (dd, J=13.9, 5.2 Hz, 1H), 3.13 (dd, J=13.9, 2.5 Hz, 1H), 1.59 (s, 9H). $^{13}$C NMR (100 MHz, CDCl$_3$) δ 174.97, 168.82, 152.75, 149.54, 147.56, 134.19, 129.71, 128.24, 127.87, 126.98, 124.24, 121.65, 113.56, 95.94, 82.53, 68.68, 61.15, 60.36, 55.88, 35.41, 28.27.

6.4 Preparation of Compound

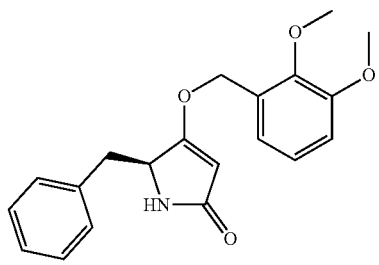 [SMILES: COc1cccc(COC2=CC(=O)N[C@H]2Cc2ccccc2)c1OC]

51071

Intermediate 20 (191 mg, 0.43 mmol) was used as raw material and the same synthesis method as in Example 1 was adopted to prepare 114 mg of the white solid of Example 6 with a yield of 78%. Molecular weight: 339.39. $^1$H NMR (400 MHz, CDCl$_3$) δ 7.23 (m, 5H), 7.11 (m, 1H), 6.97 (m, 2H), 5.70 (brs, 1H), 5.12 (s, 1H), 5.03 (m, 2H), 4.25 (dd, J=9.3, 3.5 Hz, 1H), 3.90 (s, 6H), 3.21 (dd, J=13.6, 3.6 Hz, 1H), 2.66 (dd, J=13.7, 9.3 Hz, 1H). $^{13}$C NMR (100 MHz, CDCl$_3$) δ 176.23, 173.77, 152.84, 147.57, 136.69, 129.30, 128.76, 128.59, 127.10, 124.31, 121.49, 113.36, 94.92, 68.62, 61.29, 58.89, 55.95, 38.81.

Example 7 Preparation of Compound

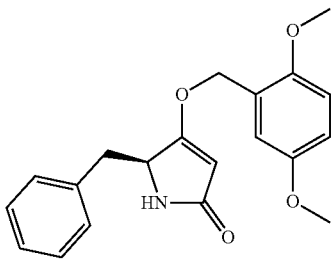 [SMILES: COc1ccc(OC)c(COC2=CC(=O)N[C@H]2Cc2ccccc2)c1]

51341

7.1 Preparation of

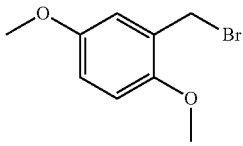

2,5-dimethoxybenzyl alcohol (1.68 g, 10 mmol) was dissolved into 50 mL of anhydrous dichloromethane, followed by stirring under ice bath for 10 minutes. Phosphorus tribromide (1.0 g, 3.7 mmol) was dropwise added slowly. Then, reaction continued under ice bath for 1 hour. After adding 200 mL of dichloromethane was added to dilute the reaction solution, water washing (50 mL×3), saturated brine washing (100 mL×1), drying with anhydrous sodium sulfate, and filtration were performed. And the solvent was removed by reduced pressure evaporation to produce a crude product, which was purified by column chromatography to obtain 2,5-dimethoxybenzyl bromide (2.2 g, yield: 96%). $^1$H NMR (400 MHz, CDCl$_3$) δ 6.91 (m, 1H), 6.82 (m, 2H), 4.54 (s, 2H), 3.85 (s, 3H), 3.77 (s, 3H). $^{13}$C NMR (100 MHz, CDCl$_3$) δ 153.43, 151.69, 126.93, 116.41, 115.07, 112.20, 56.24, 55.81, 29.07.

7.2 Preparation of

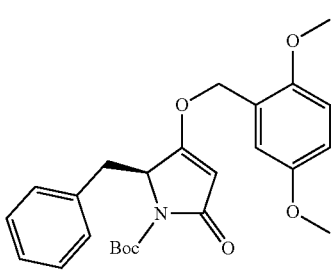 [SMILES: COc1ccc(OC)c(COC2=CC(=O)N(C(=O)OC(C)(C)C)[C@H]2Cc2ccccc2)c1]

51201, Intermediate 21

The same synthesis method as for intermediate 15 was adopted, but 2,5-dimethoxybenzyl bromide instead of 4-fluorobenzyl bromide was used to prepared intermediate 21, a colorless oily substance (247 mg, yield: 56%). Molecular weight: 439.51. $^1$H NMR (400 MHz, CDCl$_3$) δ 7.19 (m, 3H), 7.02 (m, 2H), 6.88 (m, 3H), 4.95 (s, 1H), 4.93 (s, 2H), 4.70 (dd, J=5.4, 2.8 Hz, 1H), 3.82 (s, 3H), 3.78 (s, 3H), 3.44 (dd, J=13.9, 5.2 Hz, 1H), 3.14 (dd, J=13.9, 2.8 Hz, 1H), 1.59 (s, 9H). $^{13}$C NMR (100 MHz, CDCl$_3$) δ 175.01, 168.92, 153.59, 151.54, 149.56, 134.21, 129.73, 128.22, 127.00, 123.41, 116.14, 114.59, 111.60, 95.99, 82.52, 68.53, 60.37, 55.92, 55.85, 35.41, 28.29.

7.3 Preparation of Compound

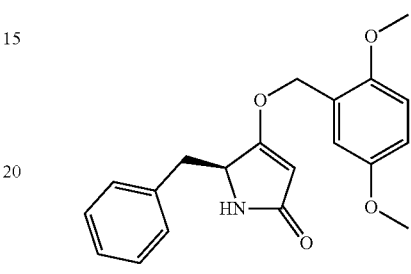

51341

Intermediate 21 (247 mg, 0.56 mmol) was used as raw material, and the same synthesis method as in Example 1 was adopted to prepare 130 mg of the white solid of Example 7 with a yield of 68%. Molecular weight: 339.39. $^1$H NMR (400 MHz, CDCl$_3$) δ 7.24 (m, 5H), 6.96 (d, J=2.5 Hz, 1H), 6.88 (m, 2H), 5.67 (s, 1H), 5.08 (s, 1H), 5.02 (m, 2H), 4.26 (dd, J=9.1, 3.6 Hz, 1H), 3.83 (s, 3H), 3.79 (s, 3H), 3.22 (dd, J=13.7, 3.6 Hz, 1H), 2.67 (dd, J=13.6, 9.1 Hz, 1H). $^{13}$C NMR (100 MHz, CDCl$_3$) δ 176.24, 173.87, 153.67, 151.47, 136.68, 129.33, 128.74, 127.09, 124.15, 115.67, 114.23, 111.63, 94.96, 68.30, 58.85, 56.05, 55.90, 38.78.

Example 8 Preparation of Compound

51221

8.1 Preparation of

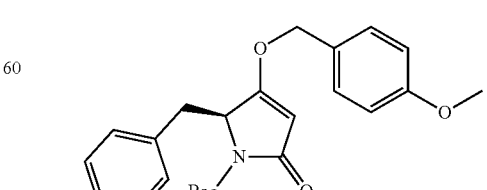

50971, Intermediate 22

The same synthesis method as for intermediate 15 was adopted, but 4-methoxybenzyl bromide was used instead of 4-fluorobenzyl bromide to prepare intermediate 22, a colorless oily substance (143 mg, yield: 35%). Molecular weight: 409.48. $^1$H NMR (400 MHz, CDCl$_3$) δ 7.30 (m, 2H), 7.20 (m, 3H), 6.97 (m, 4H), 4.91 (s, 1H), 4.83 (m, 2H), 4.69 (dd, J=5.1, 3.1 Hz, 1H), 3.84 (s, 3H), 3.43 (dd, J=14.0, 5.2 Hz, 1H), 3.12 (dd, J=14.1, 3.0 Hz, 1H), 1.59 (s, 9H). $^{13}$C NMR (100 MHz, CDCl$_3$) δ 174.97, 168.94, 160.32, 149.60, 134.32, 130.20, 129.71, 128.34, 127.10, 126.28, 114.34, 96.04, 82.70, 73.35, 60.46, 55.47, 35.49, 28.35.

8.2 Preparation of Compound

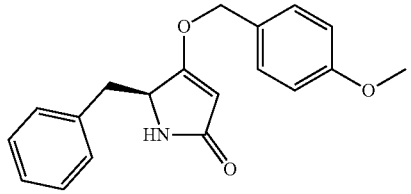 [SMILES: COc1ccc(COC2=CC(=O)N[C@H]2Cc2ccccc2)cc1]

51221

Intermediate 22 (167 mg, 0.41 mmol) was used as raw material, and the same synthesis method as in Example 1 was adopted to prepare 77 mg of the white solid of Example 8 with a yield of 61%. Molecular weight: 309.37. $^1$H NMR (400 MHz, CDCl$_3$) δ 7.29 (m, 5H), 7.18 (d, J=7.2 Hz, 2H), 6.94 (d, J=8.7 Hz, 2H), 5.66 (s, 1H), 5.06 (s, 1H), 4.92 (m, 2H), 4.24 (d, J=9.3, 3.5 Hz, 1H), 3.83 (s, 3H), 3.21 (dd, J=13.6, 3.6 Hz, 1H), 2.64 (dd, J=13.6, 9.2 Hz, 1H). $^{13}$C NMR (100 MHz, CDCl$_3$) δ 176.16, 173.75, 160.18, 136.69, 130.00, 129.29, 128.77, 127.12, 126.85, 114.29, 94.96, 73.22, 58.92, 55.46, 38.78.

Example 9 Preparation of Compound

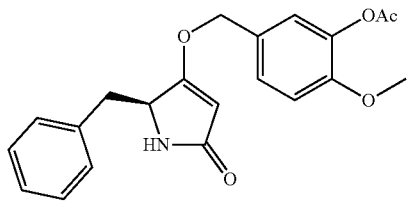 [SMILES: COc1ccc(COC2=CC(=O)N[C@H]2Cc2ccccc2)cc1OC(C)=O]

51471

9.1 Preparation of

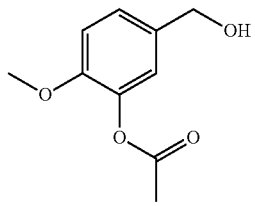

3-acetoxy-4-methoxybenzaldehyde (1.94 g, 10 mmol) was dissolved into 50 mL of anhydrous tetrahydrofuran, followed by stirring under ice bath for 10 minutes. Lithium-aluminium tetrahydride (0.19 g, 5 mmol) was added in batches followed by stirring under ice bath for 30 minutes. Saturated ammonium chloride aqueous solution was used to quench the reaction, followed by extraction with ethyl acetate three times (100 mL×3). Organic layers were combined and dried with anhydrous sodium sulfate. After filtration, the solvent was removed by reduced pressure evaporation to obtain a target product (1.9 g, yield: 97%). A next step reaction could be carried out without further purification.

9.2 Preparation of

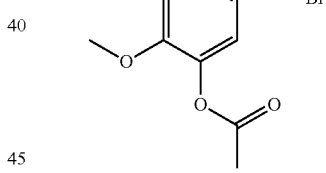

3-acetoxy-4-methoxybenzyl alcohol (1.9 g, 9.7 mmol) was dissolved into 50 mL of anhydrous dichloromethane, followed by stirring under ice bath for 10 minutes. Phosphorus tribromide (1.0 g, 3.7 mmol) was dropwise added slowly. After that, the reaction continued under ice bath for 1 hour. After 200 mL of dichloromethane was added to dilute the reaction solution, water washing (50 mL×3), saturated brine washing (100 mL×1), drying with anhydrous sodium sulfate, and filtration were performed. And the solvent was removed by reduced pressure evaporation to produce a crude product, which was purified by column chromatography to obtain 3-acetoxy-4-methoxybenzyl bromide (2.4 g, yield: 96%). $^1$H NMR (400 MHz, CDCl$_3$) δ 7.23 (dd, J=8.4, 2.2 Hz, 1H), 7.10 (d, J=2.2 Hz, 1H), 6.91 (d, J=8.4 Hz, 1H), 4.46 (s, 2H), 3.82 (s, 3H), 2.31 (s, 3H). $^{13}$C NMR (100 MHz, CDCl$_3$) δ 168.90, 151.29, 139.72, 130.35, 127.68, 123.79, 112.44, 56.05, 33.14, 20.71.

9.3 Preparation of 51371, Intermediate 23

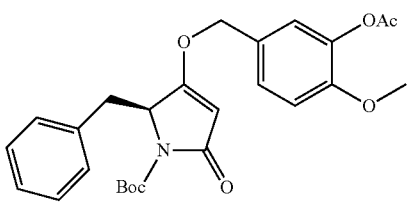 [SMILES: COc1ccc(COC2=CC(=O)N(C(=O)OC(C)(C)C)[C@H]2Cc2ccccc2)cc1OC(C)=O]

The same synthesis method as for intermediate 15 was adopted, but 3-acetoxy-4-methoxybenzyl bromide instead of 4-fluorobenzyl bromide was used to prepare intermediate 23, a colorless oily substance (176 mg, yield: 38%). Molecular weight: 467.52. $^1$H NMR (400 MHz, CDCl$_3$) δ 7.20 (m, 4H), 7.06 (s, 1H), 6.98 (m, 3H), 4.91 (s, 1H), 4.81 (m, 2H), 4.70 (dd, J=5.3, 3.0 Hz, 1H), 3.86 (s, 3H), 3.42 (dd, J=14.0, 5.3 Hz, 1H), 3.14 (dd, J=14.1, 3.0 Hz, 1H), 2.34 (s, 3H), 1.59 (s, 9H). $^{13}$C NMR (100 MHz, CDCl$_3$) δ 174.87, 168.92, 168.78, 151.82, 149.55, 140.00, 134.31, 129.68, 128.36, 127.11, 126.68, 123.13, 112.52, 96.12, 82.74, 72.70, 60.44, 56.12, 35.57, 28.34, 20.75.

9.4 Preparation of Compound 51471

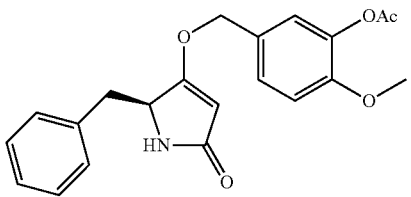 [SMILES: COc1ccc(COC2=CC(=O)N[C@H]2Cc2ccccc2)cc1OC(C)=O]

Intermediate 23 (176 mg, 0.38 mmol) was used as raw material, and the same synthesis method as in Example 1 was adopted to prepare 77 mg of the white solid of Example 9 with a yield of 56%. Molecular weight: 367.40. $^1$H NMR (400 MHz, CDCl$_3$) δ 7.24 (m, 6H), 7.10 (d, J=2.1 Hz, 1H), 7.00 (d, J=8.4 Hz, 1H), 5.38 (s, 1H), 5.07 (s, 1H), 4.89 (m, 2H), 4.24 (dd, J=9.7, 3.5 Hz, 1H), 3.87 (s, 3H), 3.22 (dd, J=13.6, 3.6 Hz, 1H), 2.62 (dd, J=13.6, 9.5 Hz, 1H), 2.34 (s, 3H). $^{13}$C NMR (100 MHz, CDCl$_3$) δ 176.07, 173.46, 169.03, 151.74, 140.02, 136.76, 129.26, 128.88, 127.27, 127.22, 127.06, 123.09, 112.53, 95.04, 72.67, 58.95, 56.16, 38.94, 20.80.

Example 10 Preparation of Compound 51351

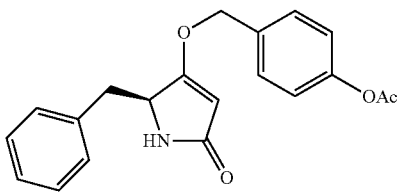 [SMILES: CC(=O)Oc1ccc(COC2=CC(=O)N[C@H]2Cc2ccccc2)cc1]

10.1 Preparation of

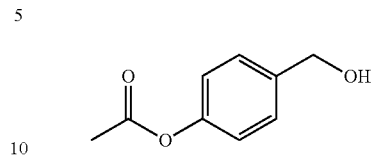

4-acetoxybenzaldehyde (1.64 g, 10 mmol) was dissolved into 50 mL of anhydrous tetrahydrofuran, followed by stirring under ice bath for 10 minutes. Lithium-aluminium tetrahydride (0.19 g, 5 mmol) was added in batches. Reaction continued for 30 minutes under stirring in ice bath before being quenched by saturated ammonium chloride aqueous solution, followed by extraction with ethyl acetate three times (100 mL×3). Organic layers were combined, and dried by anhydrous sodium sulfate. After filtration, the solvent was removed by reduced pressure evaporation to obtain the target product (1.5 g, yield: 90%). A next step reaction could be carried out without further purification.

10.2 Preparation of

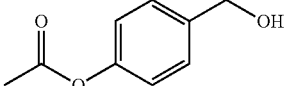

4-acetoxybenzaldehyde (1.5 g, 9.0 mmol) was dissolved into 50 mL of anhydrous dichloromethane, followed by stirring under ice bath for 10 minutes. Phosphorus tribromide (0.9 g, 3.3 mmol) was dropwise added slowly. After that reaction continued under ice bath for 1 hour. After 200 mL of dichloromethane was added to dilute the reaction solution, water washing (50 mL×3), saturated brine washing (100 mL×1), drying with anhydrous sodium sulfate, and filtration were performed. And the solvent was removed by reduced pressure evaporation to obtain a crude product, which was purified by column chromatography to obtain 3-acetoxy-4-methoxybenzyl bromide (1.8 g, yield: 87%). $^1$H NMR (400 MHz, CDCl$_3$) δ 7.40 (d, J=8.2 Hz, 2H), 7.07 (d, J=8.2 Hz, 2H), 4.48 (s, 2H), 2.30 (s, 3H). $^{13}$C NMR (100 MHz, CDCl$_3$) δ 169.36, 150.57, 135.38, 130.28, 122.01, 32.80, 21.21.

10.3 Preparation of

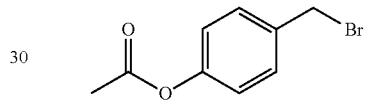

51211, Intermediate 24

The same synthesis method as for intermediate 15 was adopted, but 4-acetoxybenzyl bromide instead of 4-fluorobenzyl bromide was used to prepare 203 mg of intermediate 24, as a colorless oily substance, with a yield of 46%. Molecular weight: 437.49. $^1$H NMR (400 MHz, CDCl$_3$) δ 7.37 (d, J=8.1 Hz, 2H), 7.20 (m, 3H), 7.15 (d, J=8.1 Hz, 2H), 6.98 (m, 2H), 4.92 (s, 1H), 4.86 (m, 2H), 4.72 (t, J=4.1 Hz, 1H), 3.43 (dd, J=14.0, 5.3 Hz, 1H), 3.15 (dd, J=14.1, 3.0 Hz, 1H), 2.32 (s, 3H), 1.59 (s, 9H). $^{13}$C NMR (100 MHz, CDCl$_3$) δ 174.85, 169.36, 168.71, 151.17, 149.53, 134.29, 131.77, 129.64, 129.38, 128.38, 127.13, 122.17, 96.22, 82.77, 72.71, 60.42, 35.58, 28.33, 21.21.

10.4 Preparation of Compound

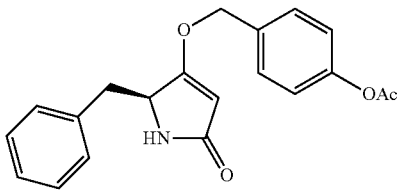 [SMILES: CC(=O)Oc1ccc(COC2=CC(=O)N[C@H]2Cc2ccccc2)cc1]

51351

Intermediate 24 (203 mg, 0.46 mmol) was used as raw material, and the same synthesis method as in Example 1 was adopted to prepare 113 mg of the white solid of Example 10 with a yield of 72%. Molecular weight: 337.38. $^1$H NMR (400 MHz, CDCl$_3$) δ 7.40 (d, J=8.5 Hz, 2H), 7.27 (m, 3H), 7.17 (m, 4H), 5.81 (s, 1H), 5.06 (s, 1H), 4.94 (m, 2H), 4.27 (dd, J=9.1, 3.7 Hz, 1H), 3.21 (dd, J=13.7, 3.7 Hz, 1H), 2.68 (dd, J=13.6, 9.0 Hz, 1H), 2.32 (s, 3H). $^{13}$C NMR (100 MHz, CDCl$_3$) δ 175.95, 173.56, 169.41, 151.04, 136.54, 132.35, 129.28, 129.27, 128.76, 127.12, 122.10, 95.19, 72.62, 58.84, 38.72, 21.22.

Example 11 Preparation of Compound

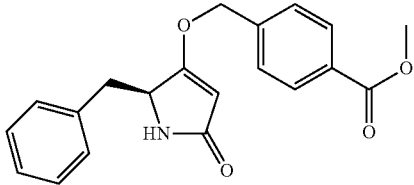 [SMILES: COC(=O)c1ccc(COC2=CC(=O)N[C@H]2Cc2ccccc2)cc1]

51321

11.1 Preparation of

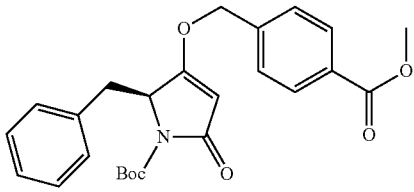 [SMILES: COC(=O)c1ccc(COC2=CC(=O)N(C(=O)OC(C)(C)C)[C@H]2Cc2ccccc2)cc1]

51181, Intermediate 25

The same synthesis method as for intermediate 15 was adopted, but methyl 4-bromomethyl benzoate was used instead of 4-fluorobenzyl bromide to prepare intermediate 25, as a colorless oily substance (169 mg, yield: 39%). Molecular weight: 437.49. $^1$H NMR (400 MHz, CDCl$_3$) δ 8.08 (d, J=7.7 Hz, 2H), 7.40 (d, J=7.8 Hz, 2H), 7.21 (m, 3H), 7.00 (m, 2H), 4.94 (m, 2H), 4.92 (s, 1H), 4.75 (dd, J=5.6, 3.1 Hz, 1H), 3.93 (s, 3H), 3.42 (dd, J=14.0, 5.4 Hz, 1H), 3.19 (dd, J=13.9, 3.1 Hz, 1H), 1.59 (s, 9H). $^{13}$C NMR (100 MHz, CDCl$_3$) δ 174.83, 168.56, 166.58, 149.50, 139.07, 134.36, 130.73, 130.18, 129.61, 128.44, 127.57, 127.18, 96.43, 82.88, 72.54, 60.44, 52.39, 35.77, 28.34.

11.2 Preparation of Compound

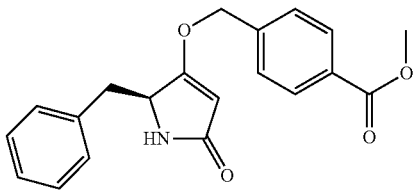 [SMILES: COC(=O)c1ccc(COC2=CC(=O)N[C@H]2Cc2ccccc2)cc1]

51321

Intermediate 25 (169 mg, 0.39 mmol) was used as raw material, and the same synthesis method as in Example 1 was adopted to prepare 93 mg of the white solid of Example 11 with a yield of 72%. Molecular weight: 337.38. $^1$H NMR (400 MHz, CDCl$_3$) δ 8.09 (d, J=8.0 Hz, 2H), 7.45 (d, J=8.0 Hz, 2H), 7.25 (m, 5H), 5.72 (s, 1H), 5.04 (m, 3H), 4.31 (dd, J=9.2, 3.7 Hz, 1H), 3.94 (s, 3H), 3.24 (dd, J=13.6, 3.8 Hz, 1H), 2.70 (dd, J=13.6, 9.1 Hz, 1H). $^{13}$C NMR (100 MHz, CDCl$_3$) δ 175.85, 173.33, 166.65, 139.68, 136.52, 130.59, 130.16, 129.26, 128.84, 127.49, 127.22, 95.48, 72.48, 58.84, 52.39, 38.85.

Example 12 Preparation of Compound

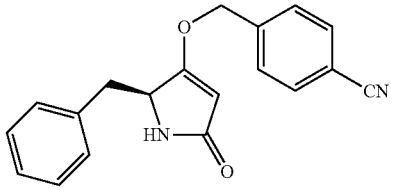 [SMILES: N#Cc1ccc(COC2=CC(=O)N[C@H]2Cc2ccccc2)cc1]

51332

12.1 Preparation of

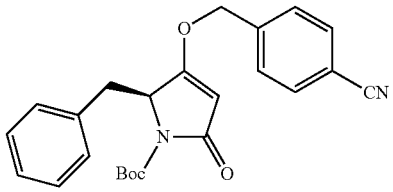 [SMILES: CC(C)(C)OC(=O)N1C(=O)C=C(OCc2ccc(C#N)cc2)[C@@H]1Cc1ccccc1]

51191, Intermediate 26

The same synthesis method as for intermediate 15 was adopted, but 4-cyanobenzyl bromide was used instead of 4-fluorobenzyl bromide to prepare intermediate 26, as a colorless oily substance (236 mg, yield: 58%). Molecular weight: 404.47. $^1$H NMR (400 MHz, CDCl$_3$) δ 7.69 (d, J=8.0 Hz, 2H), 7.41 (d, J=8.0 Hz, 2H), 7.20 (m, 3H), 6.99 (m, 2H), 4.35 (m, 2H), 4.91 (s, 1H), 4.76 (dd, J=5.7, 3.1 Hz, 1H), 3.40 (dd, J=14.0, 5.6 Hz, 1H), 3.21 (dd, J=14.1, 3.1 Hz, 1H), 1.59 (s, 9H). $^{13}$C NMR (100 MHz, CDCl$_3$) δ 174.63, 168.34, 149.40, 139.35, 134.36, 132.67, 129.51, 128.45, 128.01, 127.18, 118.33, 112.79, 96.59, 82.98, 71.95, 60.38, 35.86, 28.31.

12.2 Preparation of Compound

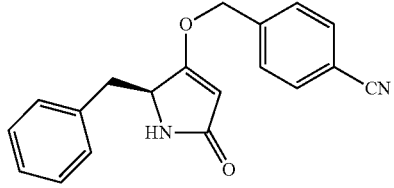 [SMILES: N#Cc1ccc(COC2=CC(=O)N[C@H]2Cc2ccccc2)cc1]

51332

Intermediate 26 (236 mg, 0.58 mmol) was used as raw material, and the same synthesis method as in Example 1 was adopted to prepare 88 mg of the white solid of Example 12 with a yield of 49%. Molecular weight: 304.35. $^1$H NMR (400 MHz, CDCl$_3$) δ 7.72 (d, J=7.9 Hz, 2H), 7.48 (d, J=7.9 Hz, 2H), 7.30 (m, 3H), 7.20 (d, J=7.2 Hz, 2H), 5.54 (s, 1H), 5.04 (m, 3H), 4.32 (dd, J=9.5, 3.7 Hz, 1H), 3.24 (dd, J=13.7, 3.8 Hz, 1H), 2.69 (dd, J=13.6, 9.3 Hz, 1H). $^{13}$C NMR (100 MHz, CDCl$_3$) δ 175.58, 172.96, 139.94, 136.47, 132.74, 129.21, 128.95, 128.03, 127.35, 118.44, 112.82, 95.73, 71.99, 58.82, 38.96.

Example 13 Preparation of Compound

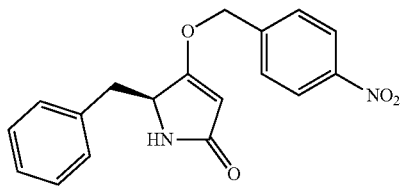

51081

13.1 Preparation of

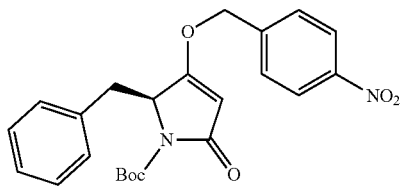 [SMILES: CC(C)(C)OC(=O)N1C(=O)C=C(OCc2ccc([N+](=O)[O-])cc2)[C@@H]1Cc1ccccc1]

51021, Intermediate 27

The same synthesis method as for intermediate 15 was adopted, but 4-nitrobenzyl bromide was used instead of 4-fluorobenzyl bromide to prepare intermediate 27, as a colorless oily substance (211 mg, yield: 50%). Molecular weight: 424.45. $^1$H NMR (400 MHz, CDCl$_3$) δ 8.26 (d, J=8.5 Hz, 2H), 7.46 (d, J=8.4 Hz, 2H), 7.22 (m, 3H), 7.02 (m, 2H), 5.00 (m, 2H), 4.95 (s, 1H), 4.79 (dd, J=5.4, 3.2 Hz, 1H), 3.41 (dd, J=14.0, 5.7 Hz, 1H), 3.24 (dd, J=14.0, 3.0 Hz, 1H), 1.60 (s, 9H). $^{13}$C NMR (100 MHz, CDCl$_3$) δ 174.66, 168.29, 149.50, 148.24, 141.24, 134.48, 129.57, 128.56, 128.12, 127.29, 124.17, 96.73, 83.11, 71.69, 60.47, 36.02, 28.38.

13.2 Preparation of Compound

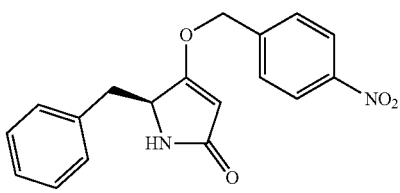 [SMILES: O=C1C=C(OCc2ccc([N+](=O)[O-])cc2)[C@H](Cc2ccccc2)N1]

51081

Intermediate 27 (211 mg, 0.50 mmol) was used as raw material, and the same synthesis method as in Example 1 was adopted to prepare 110 mg of the white solid of Example 13 with a yield of 68%. Molecular weight: 324.34. $^1$H NMR (400 MHz, CDCl$_3$) δ 8.28 (d, J=8.4 Hz, 2H), 7.54 (d, J=8.4 Hz, 2H), 7.26 (m, 5H), 5.84 (s, 1H), 5.09 (m, 2H), 5.08 (s, 1H), 4.35 (dd, J=9.0, 3.9 Hz, 1H), 3.24 (dd, J=13.7, 4.0 Hz, 1H), 2.74 (dd, J=13.7, 8.9 Hz, 1H). $^{13}$C NMR (100 MHz, CDCl$_3$) δ 175.53, 173.05, 148.14, 141.85, 136.37, 129.24, 128.88, 128.10, 127.29, 124.12, 95.82, 71.66, 58.78, 38.85.

Example 14 Preparation of Compound

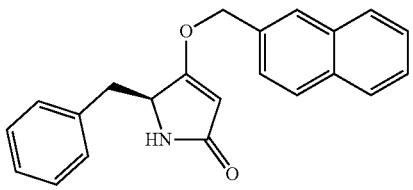 [SMILES: O=C1C=C(OCc2ccc3ccccc3c2)[C@H](Cc2ccccc2)N1]

51111

14.1 Preparation of

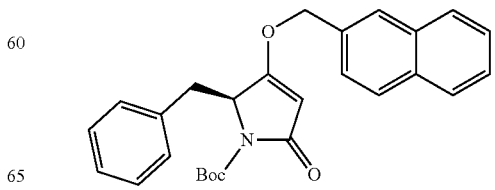

51051, Intermediate 28

The same synthesis method as for intermediate 15 was adopted, but 2-bromomethylnaphthalene instead of 4-fluorobenzyl bromide was used to prepare intermediate 28, as a colorless oily substance (70 mg, yield: 16%). Molecular weight: 429.52. $^1$H NMR (400 MHz, CDCl$_3$) δ 7.89 (m, 3H), 7.81 (s, 1H), 7.55 (m, 2H), 7.46 (d, J=8.4 Hz, 1H), 7.19 (s, 3H), 7.02 (d, J=4.3 Hz, 2H), 5.06 (m, 2H), 4.99 (s, 1H), 4.76 (s, 1H), 3.45 (dd, J=13.9, 5.2 Hz, 1H), 3.19 (dd, J=13.7, 2.2 Hz, 1H), 1.61 (s, 9H). $^{13}$C NMR (100 MHz, CDCl$_3$) δ 175.03, 168.81, 149.56, 134.35, 133.47, 133.18, 131.58, 129.69, 128.89, 128.36, 128.14, 127.90, 127.57, 127.12, 126.85, 126.76, 125.41, 96.26, 82.75, 73.59, 60.48, 35.65, 28.34.

14.2 Preparation of Compound

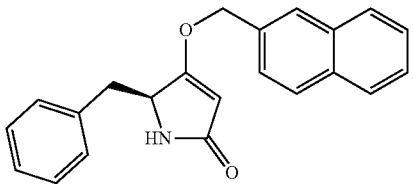 [SMILES: O=C1C=C(OCc2ccc3ccccc3c2)[C@H](Cc2ccccc2)N1]

51111

Intermediate 28 (140 mg, 0.33 mmol) was used as raw material, and the same synthesis method in Example 1 was used to prepare 94 mg of the white solid of Example 14 with a yield of 88%. Molecular weight: 329.40. $^1$H NMR (400 MHz, CDCl$_3$) δ 7.87 (m, 4H), 7.53 (m, 3H), 7.25 (m, 5H), 5.55 (s, 1H), 5.14 (m, 2H), 5.13 (s, 1H), 4.30 (dd, J=9.4, 3.5 Hz, 1H), 3.25 (dd, J=13.6, 3.6 Hz, 1H), 2.67 (dd, J=13.6, 9.3 Hz, 1H). $^{13}$C NMR (100 MHz, CDCl$_3$) δ 176.17, 173.55, 136.70, 133.47, 133.24, 132.15, 129.29, 128.88, 128.85, 128.15, 127.93, 127.47, 127.20, 126.78, 126.74, 125.43, 95.24, 73.55, 58.95, 38.93.

Example 15 Preparation of Compound

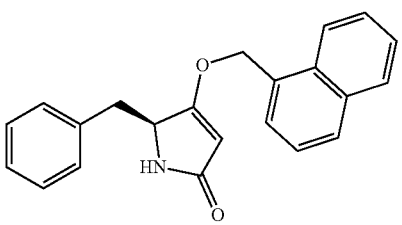 [SMILES: O=C1C=C(OCc2cccc3ccccc23)[C@H](Cc2ccccc2)N1]

51311

15.1 Preparation of

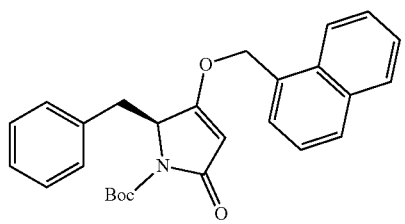 [SMILES: CC(C)(C)OC(=O)N1C(=O)C=C(OCc2cccc3ccccc23)[C@@H]1Cc1ccccc1]

51171, Intermediate 29

The same synthesis method as for intermediate 15 was adopted, but 1-bromomethylnaphthalene instead of 4-fluorobenzyl bromide was used to prepare intermediate 29, as a colorless oily substance (206 mg, yield: 48%). Molecular weight: 429.52. $^1$H NMR (400 MHz, CDCl$_3$) δ 7.96 (m, 3H), 7.61 (m, 2H), 7.50 (m, 2H), 7.17 (m, 3H), 6.94 (m, 2H), 5.33 (m, 2H), 5.08 (s, 1H), 4.73 (dd, J=5.1, 3.0 Hz, 1H), 3.43 (dd, J=14.0, 5.2 Hz, 1H), 3.08 (dd, J=14.0, 3.0 Hz, 1H). 1.60 (s, 9H). $^{13}$C NMR (100 MHz, CDCl$_3$) δ 174.91, 168.79, 149.47, 134.17, 133.84, 131.45, 130.16, 129.73, 129.65, 128.98, 128.24, 127.88, 127.01, 126.97, 126.34, 125.28, 123.31, 96.21, 82.64, 71.79, 60.41, 35.38, 28.28.

15.2 Preparation of Compound

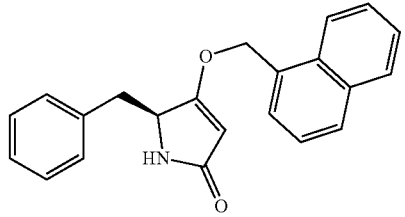 [SMILES: O=C1C=C(OCc2cccc3ccccc23)[C@H](Cc2ccccc2)N1]

51311

Intermediate 29 (206 mg, 0.48 mmol) was used as raw material, and the same synthesis method as in Example 1 was adopted to prepare 122 mg of the white solid of Example 15 with a yield of 77%. Molecular weight: 329.40. $^1$H NMR (400 MHz, CDCl$_3$) δ 7.95 (m, 3H), 7.53 (m, 4H), 7.20 (m, 5H), 5.71 (s, 1H), 5.41 (m, 2H), 5.23 (s, 1H), 4.26 (dd, J=9.2, 3.5 Hz, 1H), 3.18 (dd, J=13.6, 3.5 Hz, 1H), 2.62 (dd, J=13.6, 9.3 Hz, 1H). $^{13}$C NMR (100 MHz, CDCl$_3$) δ 176.14, 173.63, 136.63, 133.92, 131.64, 130.26, 130.12, 129.28, 129.01, 128.75, 127.83, 127.12, 126.96, 126.33, 125.33, 123.47, 95.16, 71.94, 58.96, 38.75.

Example 16 Preparation of Compound

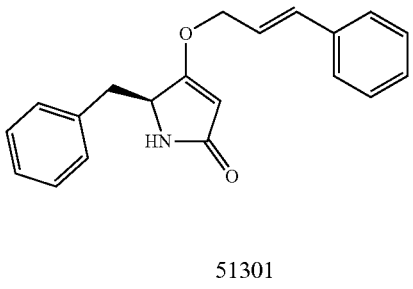

51301

16.1 Preparation of

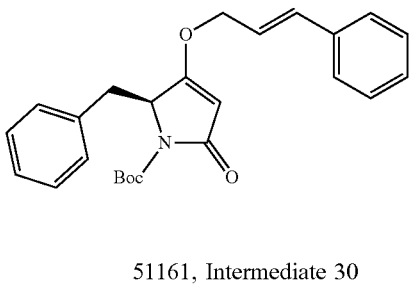

51161, Intermediate 30

The same synthesis method as for intermediate 15 was adopted, but cinnamyl bromide was used instead of 4-fluorobenzyl bromide to prepare intermediate 30, as a colorless oily substance (124 mg, yield: 31%). Molecular weight: 405.49. $^1$H NMR (400 MHz, CDCl$_3$) δ 7.38 (m, 5H), 7.20 (m, 3H), 7.04 (m, 2H), 6.70 (d, J=15.9 Hz, 1H), 6.31 (dt, J=15.9, 6.3 Hz, 1H), 4.89 (s, 1H), 4.71 (dd, J=5.2, 3.1 Hz, 1H), 4.57 (m, 2H), 3.46 (dd, J=14.0, 5.2 Hz, 1H), 3.17 (dd, J=14.0, 3.1 Hz, 1H). 1.61 (s, 9H). $^{13}$C NMR (100 MHz, CDCl$_3$) δ 174.85, 168.79, 149.51, 135.58, 135.53, 134.23, 129.66, 128.75, 128.60, 128.26, 127.04, 126.76, 121.26, 95.89, 82.65, 72.00, 60.36, 35.51, 28.28.

16.2 Preparation of Compound

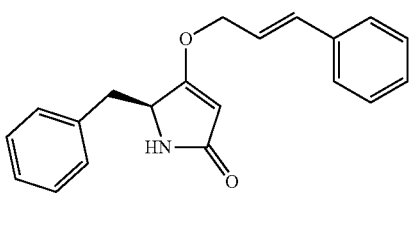 [SMILES: O=C1C=C(OC/C=C/c2ccccc2)[C@H](Cc2ccccc2)N1]

51301

Intermediate 30 (124 mg, 0.3 mmol) was used as raw material, and the same synthesis method as in Example 1 was adopted to prepare 70 mg of the white solid of Example 16 with a yield of 75%. Molecular weight: 305.38. $^1$H NMR (400 MHz, CDCl$_3$) δ 7.31 (m, 10H), 6.72 (d, J=16.0 Hz, 1H), 6.34 (dd, J=15.4, 7.0 Hz, 1H), 5.79 (s, 1H), 5.04 (s, 1H), 4.62 (m, 2H), 4.26 (d, J=8.9 Hz, 1H), 3.22 (d, J=13.7 Hz, 1H), 2.68 (dd, J=13.6, 8.9 Hz, 1H). $^{13}$C NMR (100 MHz, CDCl$_3$) δ 176.05, 173.76, 136.60, 135.84, 135.26, 129.32, 128.81, 128.75, 128.56, 127.12, 126.82, 121.91, 94.88, 72.02, 58.88, 38.76.

Example 17 Preparation of Compound

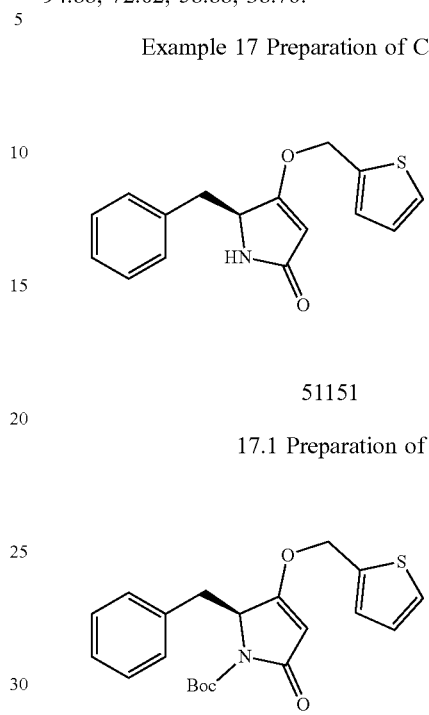

51151

17.1 Preparation of

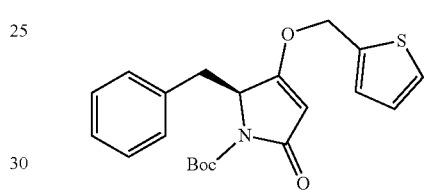

51061, Intermediate 31

The same synthesis method as for intermediate 15 was adopted, but 2-bromomethylthiophene instead of 4-fluorobenzyl bromide was used to prepare intermediate 31, as a colorless oily substance (124 mg, yield: 32%). Molecular weight: 386.48. $^1$H NMR (400 MHz, CDCl$_3$) δ 7.43 (d, J=4.9 Hz, 1H), 7.17 (m, 4H), 7.06 (m, 1H), 6.99 (m, 2H), 5.05 (m, 2H), 4.94 (s, 1H), 4.70 (m, 1H), 3.45 (dd, J=14.0, 4.9 Hz, 1H), 3.11 (dd, J=14.0, 2.5 Hz, 1H), 1.60 (s, 9H). $^{13}$C NMR (100 MHz, CDCl$_3$) δ 174.36, 168.69, 149.54, 135.87, 134.18, 129.72, 129.02, 128.36, 127.84, 127.26, 127.11, 96.24, 82.78, 67.64, 60.42, 35.39, 28.35.

17.2 Preparation of Compound

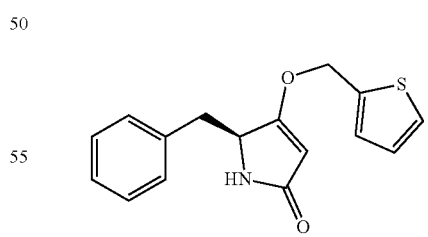

51151

Intermediate 31 (124 mg, 0.32 mmol) was used as raw material, and the same synthesis method as in Example 1 was adopted to prepare 71 mg of the white solid of Example 17 with a yield of 77%. Molecular weight: 285.36. $^1$H NMR (400 MHz, CDCl$_3$) δ 7.40 (d, J=5.0 Hz, 1H), 7.26 (m, 3H), 7.17 (m, 3H), 7.05 (t, J=3.9 Hz, 1H), 5.71 (s, 1H), 5.14 (m, 2H), 5.09 (s, 1H), 4.25 (d, J=6.5 Hz, 1H), 3.20 (dd, J=13.6, 2.6 Hz, 1H), 2.65 (dd, J=13.5, 9.2 Hz, 1H). $^{13}$C NMR (100 MHz, CDCl$_3$) δ 175.53, 173.48, 136.60, 136.55, 129.32, 128.78, 128.61, 127.53, 127.17, 127.15, 95.24, 67.71, 58.86, 38.67.

Example 18 Preparation of Compound

51571

18.1 Preparation of

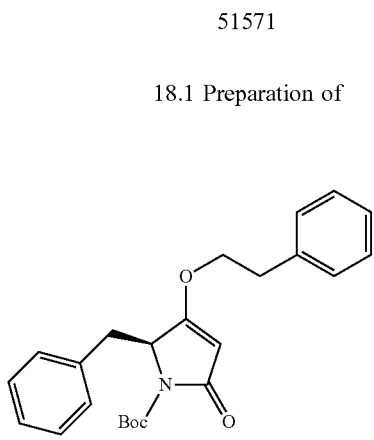

51521, Intermediate 32

The same synthesis method as for intermediate 15 was adopted, but β-bromophenylethane instead of 4-fluorobenzyl bromide was used to prepare intermediate 32, as a colorless oily substance (339 mg, yield: 86%). Molecular weight: 393.48. $^1$H NMR (400 MHz, CDCl$_3$) δ 7.36 (m, 2H), 7.26 (m, 3H), 7.10 (m, 3H), 6.68 (m, 2H), 4.76 (s, 1H), 4.64 (dd, J=5.2, 3.0 Hz, 1H), 4.13 (m, 1H), 3.95 (m, 1H), 3.38 (dd, J=13.9, 5.2 Hz, 1H), 3.07 (t, J=6.5 Hz, 2H), 3.00 (dd, J=13.9, 3.0 Hz, 1H), 1.59 (s, 9H). $^{13}$C NMR (100 MHz, CDCl$_3$) δ 175.03, 168.83, 149.50, 137.26, 134.08, 129.54, 129.07, 128.76, 128.20, 127.09, 126.90, 95.44, 82.59, 72.06, 60.27, 35.38, 35.15, 28.30.

18.2 Preparation of Compound

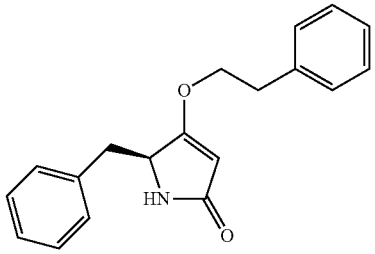 [SMILES: O=C1C=C(OCCc2ccccc2)[C@H](Cc2ccccc2)N1]

51571

Intermediate 32 (339 mg, 0.86 mmol) was used as raw material, and the same synthesis method as in Example 1 was adopted to prepare 207 mg of the white solid of Example 18 with a yield of 82%. Molecular weight: 293.37. $^1$H NMR (400 MHz, CDCl$_3$) δ 7.33 (m, 2H), 7.21 (m, 6H), 7.03 (d, J=6.9 Hz, 2H), 6.42 (s, 1H), 4.88 (s, 1H), 4.19 (dd, J=8.2, 3.8 Hz, 1H), 4.08 (m, 2H), 3.06 (m, 3H), 2.62 (dd, J=13.7, 8.1 Hz, 1H). $^{13}$C NMR (100 MHz, CDCl$_3$) δ 176.39, 137.32, 136.21, 129.33, 129.02, 128.73, 128.53, 126.96, 126.91, 94.40, 71.89, 58.79, 38.18, 35.10.

Example 19 Preparation of Compound

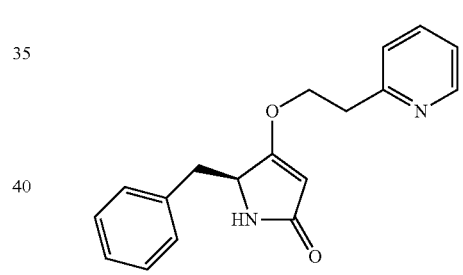

51731

19.1 Preparation of

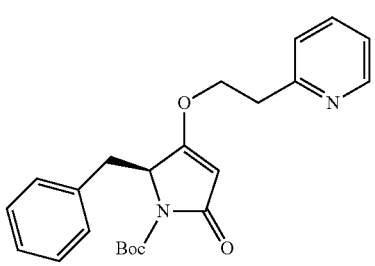 [SMILES: CC(C)(C)OC(=O)N1C(=O)C=C(OCCc2ccccn2)[C@@H]1Cc1ccccc1]

51711, Intermediate 33

The same synthesis method as for intermediate 15 was adopted, but 2-(2-bromoethyl) pyridine instead of 4-fluorobenzyl bromide to prepare intermediate 33, as a colorless oily substance (201 mg, yield: 51%). Molecular weight: 394.47. ¹H NMR (400 MHz, CDCl₃) δ 8.60 (d, J=4.0 Hz, 1H), 7.65 (td, J=7.6, 1.9 Hz, 1H), 7.15 (m, 5H), 6.72 (dd, J=6.9, 2.6 Hz, 2H), 4.82 (s, 1H), 4.60 (dd, J=5.4, 2.9 Hz, 1H), 4.29 (m, 2H), 3.34 (dd, J=13.8, 5.3 Hz, 1H), 3.23 (m, 2H), 2.96 (dd, J=13.9, 2.9 Hz, 1H), 1.57 (s, 9H). ¹³C NMR (100 MHz, CDCl₃) δ 175.02, 168.88, 157.27, 149.74, 149.54, 136.68, 134.07, 129.53, 128.25, 126.98, 123.92, 122.15, 95.63, 82.61, 70.52, 60.23, 37.26, 35.38, 28.31.

19.2 Preparation of Compound

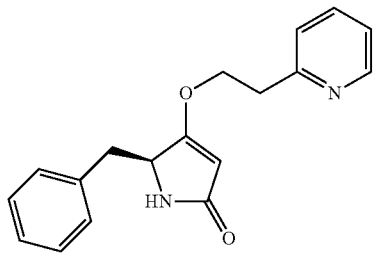 [SMILES: O=C1C=C(OCCc2ccccn2)[C@H](Cc2ccccc2)N1]

51731

Intermediate 33 (200 mg, 0.51 mmol) was used as raw material, and the same synthesis method as in Example 1 was adopted to prepare 86 mg of the white solid of Example 19 with a yield of 58%. Molecular weight: 294.35. ¹H NMR (400 MHz, CDCl₃) δ 8.59 (d, J=4.3 Hz, 1H), 7.65 (td, J=7.7, 1.9 Hz, 1H), 7.22 (m, 5H), 7.06 (m, 2H), 5.95 (s, 1H), 4.96 (s, 1H), 4.34 (m, 2H), 4.18 (dd, J=8.8, 3.8 Hz, 1H), 3.26 (t, J=6.6 Hz, 2H), 3.05 (dd, J=13.7, 3.8 Hz, 1H), 2.56 (dd, J=13.7, 8.6 Hz, 1H). ¹³C NMR (100 MHz, CDCl₃) δ 176.32, 174.13, 157.43, 149.69, 136.70, 136.39, 129.27, 128.66, 127.03, 123.78, 122.06, 94.49, 70.46, 58.73, 38.45, 37.29.

Example 20 Preparation of Compound 51551

20.1 Preparation of

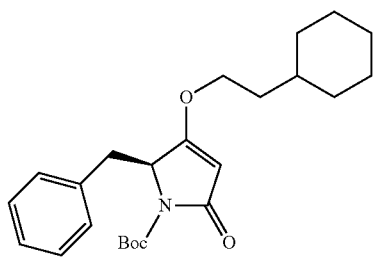 [SMILES: CC(C)(C)OC(=O)N1C(=O)C=C(OCCC2CCCCC2)[C@@H]1Cc1ccccc1]

51501, Intermediate 34

The same synthesis method as for intermediate 15 was adopted, but 2-cyclohexyl ethyl bromide instead of 4-fluorobenzyl bromide to prepare intermediate 34, as a colorless oily substance, (341 mg, yield: 85%). Molecular weight: 399.53. ¹H NMR (400 MHz, CDCl₃) δ 7.20 (m, 3H), 7.00 (m, 2H), 4.78 (s, 1H), 4.66 (dd, J=5.4, 3.0 Hz, 1H), 3.89 (m, 2H), 3.43 (dd, J=14.0, 5.3 Hz, 1H), 3.13 (dd, J=14.0, 3.0 Hz, 1H), 1.68 (m, 7H), 1.59 (s, 9H), 1.45 (m, 1H), 1.25 (m, 3H), 0.96 (m, 2H). ¹³C NMR (100 MHz, CDCl₃) δ 175.51, 169.09, 149.65, 134.42, 129.65, 128.31, 127.08, 95.28, 82.63, 69.68, 60.38, 35.99, 35.59, 34.34, 33.36, 33.06, 28.37, 26.49, 26.25, 26.20.

20.2 Preparation of Compound

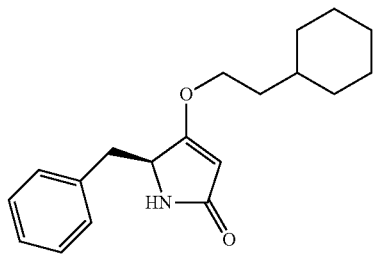 [SMILES: O=C1C=C(OCCC2CCCCC2)[C@H](Cc2ccccc2)N1]

51551

Intermediate 34 (341 mg, 0.85 mmol) was used as raw material, and the same synthesis method as in Example 1 was adopted to prepare 216 mg of the white solid of Example 20 with a yield was 84%. Molecular weight: 299.41. ¹H NMR (400 MHz, CDCl₃) δ 7.24 (m, 5H), 5.75 (s, 1H), 4.93 (s, 1H), 4.21 (dd, J=9.0, 3.6 Hz, 1H), 3.96 (m, 2H), 3.18 (dd, J=13.7, 3.7 Hz, 1H), 2.65 (dd, J=13.6, 9.0 Hz, 1H), 1.71 (m, 7H), 1.46 (m, 1H), 1.25 (m, 3H), 0.97 (m, 2H). ¹³C NMR (100 MHz, CDCl₃) δ 176.65, 174.03, 136.69, 129.30, 128.71, 127.08, 94.07, 69.70, 58.79, 38.75, 35.97, 34.51, 33.34, 33.18, 26.52, 26.26.

Example 21 Preparation of Compound

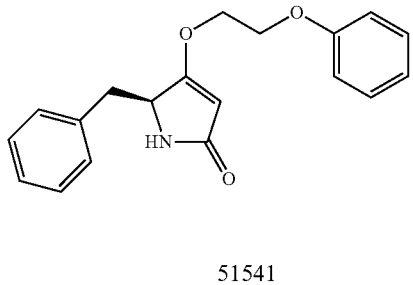

51541

21.1 Preparation of

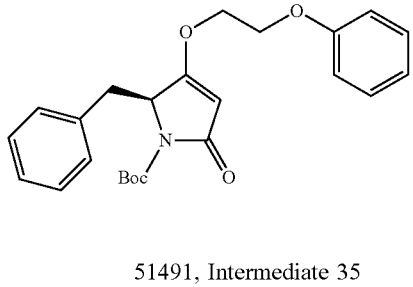

51491, Intermediate 35

The same synthesis method as for intermediate 15 was adopted, but 2-phenoxyethyl bromide instead of 4-fluorobenzyl bromide was used to prepare intermediate 35, as a colorless oily substance (309 mg, yield: 75%). Molecular weight: 409.48. $^1$H NMR (400 MHz, CDCl$_3$) δ 7.33 (t, J=7.7 Hz, 2H), 7.15 (m, 3H), 7.05 (m, 3H), 6.95 (d, J=8.1 Hz, 2H), 4.86 (s, 1H), 4.71 (dd, J=5.1, 3.0 Hz, 1H), 4.30 (m, 3H), 4.17 (m, 1H), 3.46 (dd, J=13.9, 5.1 Hz, 1H), 3.16 (dd, J=13.9, 2.9 Hz, 1H), 1.61 (s, 9H). $^{13}$C NMR (100 MHz, CDCl$_3$) δ 174.93, 168.70, 158.22, 149.57, 134.15, 129.79, 128.34, 127.11, 121.61, 114.57, 95.93, 82.78, 69.94, 65.32, 60.39, 35.41, 28.37.

21.2 Preparation of Compound

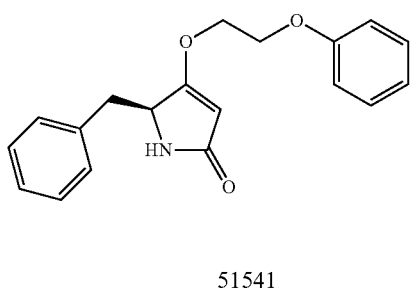

51541

Intermediate 35 (309 mg, 0.76 mmol) was used as raw material, and the same synthesis method as in Example 1 was adopted to prepare 215 mg of the white solid of Example 21 with a yield of 92%. Molecular weight: 309.37. $^1$H NMR (400 MHz, CDCl$_3$) δ 7.32 (t, J=7.8 Hz, 2H), 7.21 (m, 5H), 6.97 (m, 3H), 6.25 (s, 1H), 4.99 (s, 1H), 4.27 (m, 5H), 3.15 (dd, J=13.7, 3.8 Hz, 1H), 2.73 (dd, J=13.7, 8.0 Hz, 1H). $^{13}$C NMR (100 MHz, CDCl$_3$) δ 175.97, 173.75, 158.32, 136.17, 129.69, 129.44, 128.53, 126.98, 121.48, 114.64, 94.90, 69.79, 65.52, 58.59, 38.27.

Example 22 Preparation of Compound

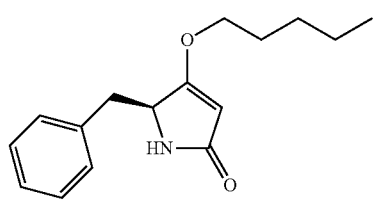 [SMILES: CCCCCOC1=CC(=O)N[C@H]1Cc1ccccc1]

51561

22.1 Preparation of

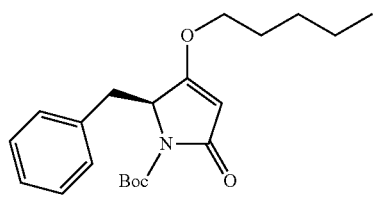 [SMILES: CCCCCOC1=CC(=O)N(C(=O)OC(C)(C)C)[C@H]1Cc1ccccc1]

51511, Intermediate 36

The same synthesis method as for intermediate 15 was adopted, but 1-bromopentane instead of 4-fluorobenzyl bromide was used to prepare intermediate 36, as a colorless oily substance (299 mg, yield: 83%). Molecular weight: 359.47. $^1$H NMR (400 MHz, CDCl$_3$) δ 7.19 (m, 3H), 6.99 (m, 2H), 4.78 (s, 1H), 4.66 (dd, J=5.4, 3.0 Hz, 1H), 3.85 (m, 2H), 3.42 (dd, J=14.0, 5.3 Hz, 1H), 3.14 (dd, J=14.0, 3.0 Hz, 1H), 1.78 (m, 2H), 1.59 (s, 9H), 1.40 (m, 4H), 0.94 (t, J=6.9 Hz, 3H). $^{13}$C NMR (100 MHz, CDCl$_3$) δ 175.50, 169.06, 149.62, 134.40, 129.64, 128.30, 127.07, 95.26, 82.60, 71.68, 60.36, 35.61, 28.35, 28.33, 28.07, 22.36, 14.01.

22.2 Preparation of Compound

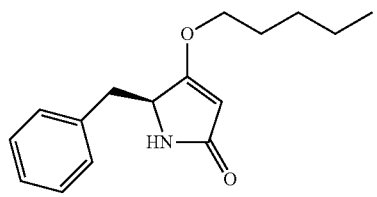 [SMILES: CCCCCOC1=CC(=O)N[C@H]1Cc1ccccc1]

51561

Intermediate 36 (299 mg, 0.83 mmol) was used as raw material, and the same synthesis method as in Example 1 was adopted to prepare 210 mg of the white solid of Example 22 with a yield of 97%. Molecular weight: 259.35. $^1$H NMR (400 MHz, CDCl$_3$) δ 7.24 (m, 5H), 5.74 (s, 1H), 4.93 (s, 1H), 4.22 (dd, J=9.2, 3.6 Hz, 1H), 3.93 (m, 2H), 3.19 (dd, J=13.7, 3.6 Hz, 1H), 2.65 (dd, J=13.6, 9.0 Hz, 1H), 1.78 (m, 2H), 1.41 (m, 4H), 0.95 (t, J=6.8 Hz, 3H). $^{13}$C NMR (100 MHz, CDCl$_3$) δ 176.67, 174.04, 136.72, 129.29, 128.72, 127.07, 94.05, 71.63, 58.81, 38.79, 28.35, 28.10, 22.42, 14.06.

Example 23 Preparation of Compound

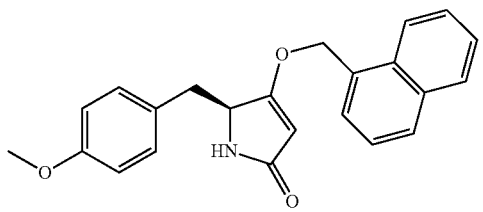 [SMILES: COc1ccc(C[C@@H]2NC(=O)C=C2OCc2cccc3ccccc23)cc1]

60231

23.1 Preparation of

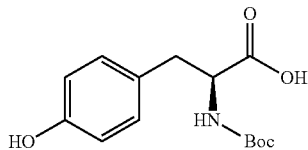 [SMILES: CC(C)(C)OC(=O)N[C@@H](Cc1ccc(O)cc1)C(=O)O]

Intermediate 10

L-tyrosine (10 g, 55.2 mmol) was dissolved into 300 mL of a mixture solution of 1,4-dioxane and water (v/v 1:1). Triethylamine (11.2 g, 110.7 mmol) and di-tert-butyl dicarbonate (13.3 g, 60.9 mmol) were added in turn at room temperature, followed by stirring for 10 hours at room temperature. After the reaction was completed as monitored by TLC, 1,4-dioxane was removed by reduced pressure evaporation, and 500 mL of dichloromethane was added. 2N hydrochloric acid solution was added dropwise under stirring until the pH value of the water layer was about 5. The organic layer was separated, washed once with 200 mL of saturated brine, and dried with anhydrous magnesium sulfate. After filtration, the solvent was removed by reduced pressure evaporation to obtain a crude product with a yield of 99%. A next reaction could be carried out without further purification.

23.2 Preparation of

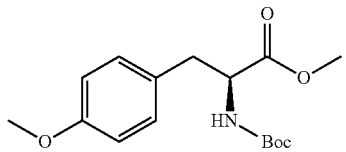

Intermediate 11

Intermediate 10 (7.7 g, 27.4 mmol) was dissolved into 100 mL of N,N-dimethylformamide, followed by stirring under ice bath for 10 minutes. Potassium carbonate (8.3 g, 60.1 mmol) and iodomethane (7.8 g, 55.0 mmol) were added in turn, followed by stirring under ice bath for 30 minutes and stirring overnight at room temperature. The reaction liquid was poured into 300 mL of ethyl acetate, washed twice with water (300 mL×2), washed once with saturated brine (100 mL×1), and dried with anhydrous sodium sulfate. After filtration, the solvent was removed by evaporation to obtain a crude product, which went through column chromatography for separation and purification to obtain the target product with a yield of 89%. $^1$H NMR (400 MHz, CDCl$_3$) δ 7.03 (d, J=8.6 Hz, 2H), 6.82 (d, J=8.7 Hz, 2H), 6.82 (d, J=8.7 Hz, 2H), 4.96 (d, J=8.3 Hz, 1H), 4.54 (m, 1H), 3.78 (s, 3H), 3.71 (s, 3H), 3.02 (m, 2H), 1.42 (m, 9H). $^{13}$C NMR (100 MHz, CDCl$_3$) δ 172.56, 158.75, 155.22, 130.40, 128.03, 114.08, 80.02, 55.35, 54.65, 52.33, 37.58, 28.43.

23.3 Preparation of

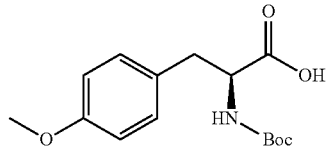 [SMILES: COc1ccc(C[C@H](NC(=O)OC(C)(C)C)C(=O)O)cc1]

Intermediate 12

Intermediate 11 (8.5 g, 27.5 mmol) was dissolved into a mixture of 200 mL of methanol and water (v/v 1:1). Sodium hydroxide (4.4 g, 110 mmol) was added in batches at room temperature, followed by stirring overnight at room temperature. 10% hydrochloric acid solution was added to adjust the pH value to about 5, followed by extraction with 500 mL of dichloromethane. The organic layer was washed with 100 mL of saturated brine once, which preceded drying with anhydrous sodium sulphate. After filtration, the solvent was removed by reduced pressure evaporation to obtain the target product with a yield of 95%. A next step reaction could be carried out without further purification.

23.4 Preparation of

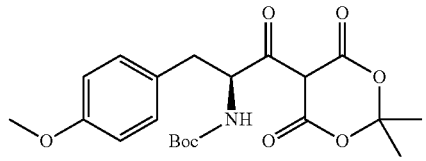

Intermediate 13

The same synthesis method as for intermediate 2 was used, the yield being 85%. A next step reaction could be carried out without further purifying the product.

23.5 Preparation of

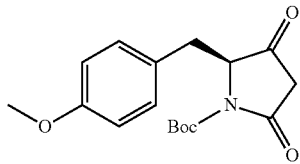 [SMILES: COc1ccc(C[C@H]2C(=O)CC(=O)N2C(=O)OC(C)(C)C)cc1]

Intermediate 14

The same synthesis method as for intermediate 3 was adopted, with a yield of 90%.

23.6 Preparation of

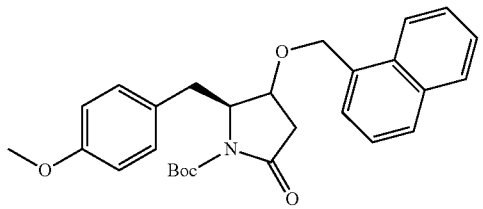 [SMILES: COc1ccc(C[C@H]2C(OCc3cccc4ccccc34)CC(=O)N2C(=O)OC(C)(C)C)cc1]

60171, Intermediate 37

Intermediate 14 (1.97 g, 6.2 mmol) was dissolved into 30 mL of acetonitrile. K$_2$CO$_3$ (937 mg, 6.78 mmol) and 1-bromomethyl naphthalene (1.5 g, 6.78 mmol) were added successively at room temperature, followed by reflux reaction for 5 hours. After cooling to room temperature, solids were removed by filtration. The filtrate was dried by evaporation, and went through column chromatography for purification to obtain intermediate 37, as a colorless oily substance (522 mg, yield: 18%). Molecular weight: 459.54. $^1$H NMR (400 MHz, CDCl$_3$) δ 7.99 (d, J=8.2 Hz, 1H), 7.94 (d, J=7.7 Hz, 2H), 7.53 (m, 4H), 6.82 (d, J=8.5 Hz, 2H), 6.69 (d, J=8.5 Hz, 2H), 5.36 (dd, J=66.5, 11.5 Hz, 2H), 5.08 (s, 1H), 4.69 (dd, J=5.1, 2.9 Hz, 1H), 3.75 (s, 3H), 3.37 (dd, J=14.2, 5.1 Hz, 1H), 3.02 (dd, J=14.2, 3.0 Hz, 1H), 1.60 (s, 9H). $^{13}$C NMR (100 MHz, CDCl$_3$) δ 175.02, 168.95, 158.59, 149.50, 133.89, 131.50, 130.65, 130.21, 129.79, 129.02, 127.94, 127.01, 126.39, 126.04, 125.32, 123.36, 113.69, 96.30, 82.65, 71.82, 60.60, 55.19, 34.49, 28.33.

23.7 Preparation of Compound

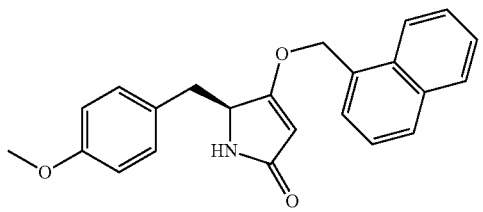 [SMILES: COc1ccc(C[C@@H]2NC(=O)C=C2OCc2cccc3ccccc23)cc1]

60231

Intermediate 37 (522 mg, 1.34 mmol) was used as raw material, and the same synthesis method as in Example 1 was adopted to prepare 268 mg of the white solid of Example 23 with a yield of 66%. Molecular weight: 359.43. $^1$H NMR (400 MHz, CDCl$_3$) δ 7.99 (d, J=8.2 Hz, 1H), 7.93 (d, J=7.5 Hz, 2H), 7.55 (m, 4H), 7.06 (d, J=8.5 Hz, 2H), 6.80 (d, J=8.6 Hz, 2H), 5.65 (d, J=9.5 Hz, 1H), 5.42 (m, 2H), 5.22 (s, 1H), 4.23 (dd, J=9.1, 3.5 Hz, 1H), 3.77 (s, 3H), 3.12 (dd, J=13.8, 3.6 Hz, 1H), 2.59 (dd, J=13.8, 9.1 Hz, 1H). $^{13}$C NMR (100 MHz, CDCl$_3$) δ 176.22, 173.66, 158.75, 133.94, 131.66, 130.31, 130.28, 130.12, 129.01, 128.52, 127.82, 126.97, 126.34, 125.34, 123.49, 114.17, 95.15, 71.91, 59.14, 55.36, 37.88.

Example 24 Preparation of Compound

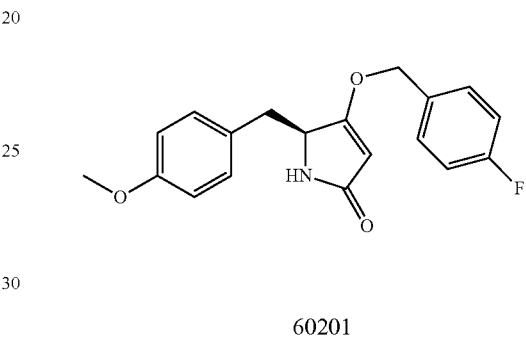

60201

24.1 Preparation of

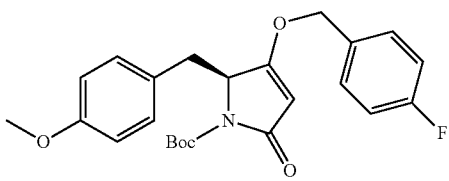 [SMILES: COc1ccc(C[C@H]2C(OCc3ccc(F)cc3)=CC(=O)N2C(=O)OC(C)(C)C)cc1]

60141, Intermediate 38

Intermediate 14 (1.16 g, 3.6 mmol) was dissolved into 20 mL of acetonitrile. K$_2$CO$_3$ (552 mg, 4.0 mmol) and 4-fluorobenzyl bromide (755 mg, 4.0 mmol) were added successively at room temperature, followed by reflux reaction for 5 hours. After cooling to room temperature, solids were removed by filtration, and the filtrate was dried by evaporation, and went through column chromatography for purification to obtain intermediate 38, as a colorless oily substance (324 mg, yield: 21%). Molecular weight: 427.47. $^1$H NMR (400 MHz, CDCl$_3$) δ 7.34 (m, 2H), 7.11 (t, J=8.6 Hz, 2H), 6.88 (d, J=8.6 Hz, 2H), 6.72 (d, J=8.6 Hz, 2H), 4.91 (s, 1H), 4.85 (m, 2H), 4.66 (dd, J=5.1, 2.9 Hz, 1H), 3.74 (s, 3H), 3.38 (dd, J=14.2, 5.2 Hz, 1H), 3.07 (dd, J=14.2, 3.0 Hz, 1H), 1.59 (s, 9H). $^{13}$C NMR (100 MHz, CDCl$_3$) δ 174.84, 168.86, 163.07 (d, J=248.3 Hz), 158.61, 149.46, 130.56, 130.24 (d, J=8.4 Hz), 130.08 (d, J=3.4 Hz), 126.05, 115.94 (d, J=21.8 Hz), 113.74, 96.25, 82.73, 72.63, 60.51, 55.18, 34.58, 28.31. $^{19}$F NMR (376 MHz, CDCl$_3$) δ −112.18.

24.2 Preparation of Compound

60201

Intermediate 38 (324 mg, 0.76 mmol) was used as raw material, and the same synthesis method as in Example 1 was adopted to prepare 140 mg of the white solid of Example 24 with a yield of 56%. Molecular weight: 327.36. $^1$H NMR (400 MHz, CDCl$_3$) δ 7.37 (m, 2H), 7.11 (m, 4H), 6.83 (d, J=8.2 Hz, 2H), 5.44 (s, 1H), 5.06 (s, 1H), 4.93 (m, 1H), 4.22 (dd, J=9.4, 3.5 Hz, 1H), 3.79 (s, 3H), 3.15 (dd, J=13.8, 3.7 Hz, 1H), 2.59 (dd, J=13.8, 9.2 Hz, 1H). $^{13}$C NMR (100 MHz, CDCl$_3$) δ 175.97, 173.78, 162.98 (d, J=247.9 Hz), 158.67, 130.62 (d, J=33 Hz, 130.29, 130.06 (d, J=8.3 Hz), 128.29, 115.86 (d, J=21.7 Hz), 114.07, 95.20, 72.53, 58.99, 55.31, 37.68. $^{19}$F NMR (376 MHz, CDCl$_3$) δ −112.59.

Example 25 Preparation of Compound

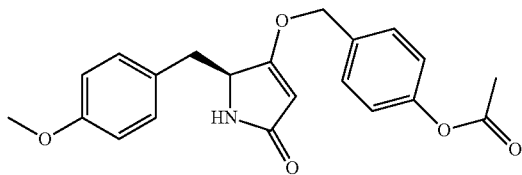 [SMILES: COc1ccc(C[C@@H]2NC(=O)C=C2OCc2ccc(OC(C)=O)cc2)cc1]

60111

25.1 Preparation of

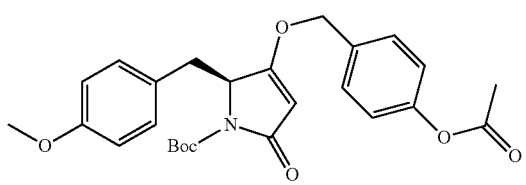 [SMILES: COc1ccc(C[C@H]2C(OCc3ccc(OC(C)=O)cc3)=CC(=O)N2C(=O)OC(C)(C)C)cc1]

60051, Intermediate 39

Intermediate 14 (638 mg, 2.0 mmol) was dissolved into 10 mL of acetonitrile. K$_2$CO$_3$ (304 mg, 2.2 mmol) and 4-acetoxybenzyl bromide (504 mg, 2.2 mmol) were added successively at room temperature, followed by reflux reaction for 5 hours. After cooling to room temperature, solids were removed by filtration, and the filtrate was evaporated by evaporation, and went through column chromatography for purification to obtain intermediate 39, as a colorless oily substance (307 mg, yield: 33%). Molecular weight: 467.52. $^1$H NMR (400 MHz, CDCl$_3$) δ 7.38 (d, J=8.4 Hz, 2H), 7.15 (d, J=8.5 Hz, 2H), 6.88 (d, J=8.6 Hz, 2H), 6.73 (d, J=8.6 Hz, 2H), 4.92 (s, 1H), 4.88 (m, 2H), 4.67 (dd, J=5.1, 2.9 Hz, 1H), 3.75 (s, 3H), 3.39 (dd, J=14.2, 5.1 Hz, 1H), 3.08 (dd, J=14.2, 3.0 Hz, 1H), 2.32 (s, 3H), 1.59 (s, 9H). $^{13}$C NMR (100 MHz, CDCl$_3$) δ 174.90, 169.37, 168.85, 158.68, 151.19, 149.53, 131.80, 130.61, 129.41, 126.09, 122.19, 113.81, 96.30, 82.74, 72.70, 60.57, 55.23, 34.62, 28.35, 21.22.

25.2 Preparation of Compound

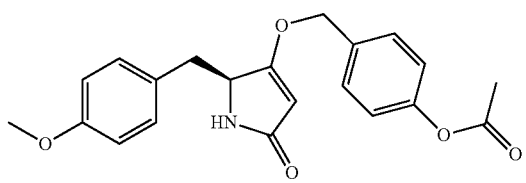 [SMILES: COc1ccc(C[C@@H]2NC(=O)C=C2OCc2ccc(OC(C)=O)cc2)cc1]

60111

Intermediate 39 (307 mg, 0.66 mmol) was used as raw material, and the same synthesis method as in Example 1 was adopted to prepare 160 mg of the white solid of Example 25 with a yield of 66%. Molecular weight: 367.40. $^1$H NMR (400 MHz, CDCl$_3$) δ 7.40 (d, J=8.4 Hz, 2H), 7.14 (d, J=8.4 Hz, 2H), 7.09 (d, J=8.5 Hz, 1H), 6.82 (d, J=8.5 Hz, 1H), 5.64 (s, 1H), 5.05 (s, 1H), 4.96 (m, 2H), 4.22 (dd, J=9.0, 3.6 Hz, 1H), 3.78 (s, 3H), 3.14 (dd, J=13.8, 3.6 Hz, 1H), 2.62 (dd, J=13.8, 9.0 Hz, 1H), 2.32 (s, 3H). $^{13}$C NMR (100 MHz, CDCl$_3$) δ 176.03, 173.56, 169.43, 158.77, 151.06, 132.38, 130.28, 129.29, 128.45, 122.12, 114.20, 95.19, 72.63, 59.04, 55.37, 37.87, 21.25.

Example 26 Preparation of Compound

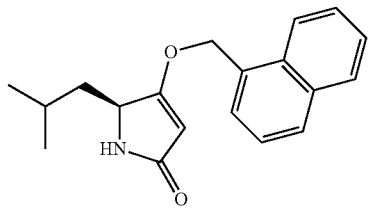 [SMILES: CC(C)C[C@@H]1NC(=O)C=C1OCc1cccc2ccccc12]

60241

26.1 Preparation of

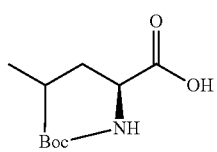

Intermediate 4

The synthesis method for intermediate 1 was adopted, and L-leucine was used as raw material, the yield being 99%. A next step reaction could be carried out without further purifying the product.

26.2 Preparation of

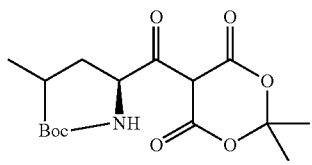 [SMILES: CCC[C@H](NC(=O)OC(C)(C)C)C(=O)C1C(=O)OC(C)(C)OC1=O]

Intermediate 5

The same synthesis method as for intermediate 2 was adopted, the yield being 82%. A next step reaction could be carried out without further purifying the product.

26.3 Preparation of

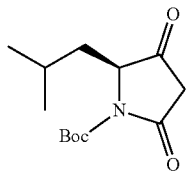 [SMILES: CC(C)C[C@H]1C(=O)CC(=O)N1C(=O)OC(C)(C)C]

Intermediate 6

The same synthesis method as for intermediate 3 was adopted, and a crude product went through column chromatography for separation and purification to obtain the target product with a yield of 77%.

26.4 Preparation of

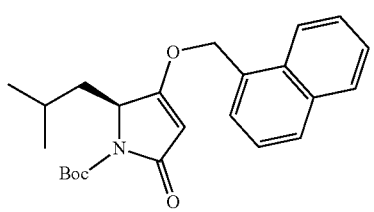 [SMILES: CC(C)C[C@H]1C(OCc2cccc3ccccc23)=CC(=O)N1C(=O)OC(C)(C)C]

60181, Intermediate 40

Intermediate 6 (400 mg, 1.57 mmol) was dissolved into 5 mL of acetonitrile. $K_2CO_3$ (238 mg, 1.72 mmol) and 1-bromomethylnaphthalene (381 mg, 1.72 mmol) were added in turn at room temperature, followed by reflux reaction for 5 hours. After cooling to room temperature, solids were removed by filtration, and the filtrate was dried by evaporation, and went through column chromatography for purification to obtain intermediate 40, as a colorless oily substance (138 mg, yield: 22%). Molecular weight: 395.5. $^1$H NMR (400 MHz, CDCl$_3$) δ 7.90 (m, 3H), 7.51 (m, 4H), 5.40 (s, 2H), 5.27 (s, 1H), 4.48 (dd, J=6.8, 3.0 Hz, 1H), 1.76 (m, 3H), 1.53 (s, 9H), 0.82 (t, J=6.4 Hz, 6H). $^{13}$C NMR (100 MHz, CDCl$_3$) δ 177.24, 169.38, 149.27, 133.82, 131.46, 130.17, 129.73, 128.92, 127.82, 126.87, 126.28, 125.19, 123.32, 95.07, 82.50, 72.12, 59.35, 39.34, 28.23, 23.91, 23.79, 23.02.

26.5 Preparation of Compound

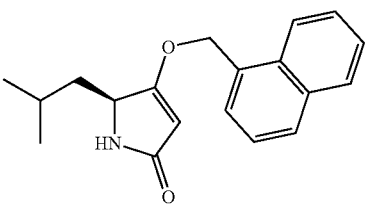 [SMILES: CC(C)C[C@@H]1NC(=O)C=C1OCc1cccc2ccccc12]

60241

Intermediate 40 (138 mg, 0.35 mmol) was used as raw material, and the same synthesis method as in Example 1 was adopted to prepare 65 mg of the white solid of Example 26 with a yield of 63%. Molecular weight: 295.38. $^1$H NMR (400 MHz, CDCl$_3$) δ 7.92 (m, 3H), 7.52 (m, 4H), 6.63 (s, 1H), 5.40 (s, 2H), 5.23 (s, 1H), 4.12 (dd, J=9.8, 3.5 Hz, 1H), 1.76 (m, 1H), 1.64 (m, 1H), 1.40 (m, 1H), 0.91 (d, J=6.3 Hz, 6H). $^{13}$C NMR (100 MHz, CDCl$_3$) δ 177.80, 174.53, 133.91, 131.63, 130.42, 130.00, 128.95, 127.62, 126.86, 126.28, 125.30, 123.51, 94.42, 71.88, 56.53, 41.57, 25.61, 23.61, 21.88.

Example 27 Preparation of Compound

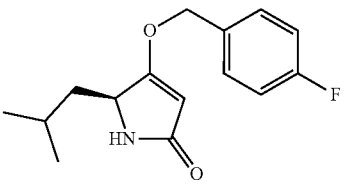 [SMILES: CC(C)C[C@@H]1NC(=O)C=C1OCc1ccc(F)cc1]

60211

27.1 Preparation of

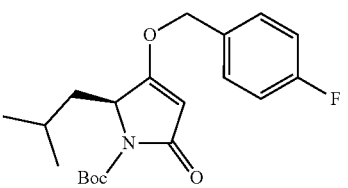 [SMILES: CC(C)C[C@H]1C(OCc2ccc(F)cc2)=CC(=O)N1C(=O)OC(C)(C)C]

60151, Intermediate 41

Intermediate 6 (1.0 g, 3.92 mmol) was dissolved into 20 mL of acetonitrile. K₂CO₃ (595 mg, 4.31 mmol) and 4-fluorobenzyl bromide (815 mg, 4.31 mmol) were added in turn at room temperature, followed by reflux reaction for 5 hours. After cooling to room temperature, solids were removed by filtration, and the filtrate was dried by evaporation and went through column chromatography for purification to obtain intermediate 41, as a colorless oily substance (304 mg, yield: 21%). Molecular weight: 363.43. $^1$H NMR (400 MHz, CDCl₃) δ 7.32 (m, 2H), 7.07 (m, 2H), 5.10 (s, 1H), 4.95 (m, 2H), 4.48 (dd, J=6.8, 3.1 Hz, 1H), 1.78 (m, 3H), 1.51 (s, 9H), 0.87 (d, J=6.3 Hz, 6H). $^{13}$C NMR (100 MHz, CDCl₃) δ 177.09, 169.27, 163.00 (d, J=248.1 Hz), 149.28, 130.19 (d, J=3.4 Hz), 129.92 (d, J=8.4 Hz), 115.90 (d, J=21.7 Hz). 95.14, 82.60, 72.73, 59.28, 39.46, 28.24, 24.02, 23.82, 23.08. $^{19}$F NMR (376 MHz, CDCl₃) δ −112.38.

27.2 Preparation of Compound

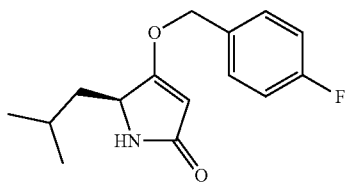

60211

Intermediate 41 (304 mg, 0.84 mmol) was used as raw material, and the same synthesis method as in Example 1 was adopted to prepare 156 mg of the white solid of Example 27 with a yield of 71%. Molecular weight: 263.31. $^1$H NMR (400 MHz, CDCl₃) δ 7.33 (m, 2H), 7.08 (t, J=8.4 Hz, 2H), 6.70 (s, 1H), 5.06 (s, 1H), 4.93 (m, 2H), 4.10 (dd, J=9.9, 3.4 Hz, 1H), 2.00 (s, 1H), 1.76 (m, 1H), 1.65 (m, 1H), 1.39 (m, 1H), 0.94 (d, J=6.6 Hz, 6H). $^{13}$C NMR (100 MHz, CDCl₃) δ 177.60, 174.52, 162.97 (d, J=247.8 Hz), 130.78 (d, J=3.2 Hz), 129.89 (d, J=8.3 Hz), 115.85 (d, J=21.8 Hz), 94.43, 72.49, 56.44, 41.56, 25.59, 23.65, 21.87. $^{19}$F NMR (376 MHz, CDCl₃) δ −112.84.

Example 28 Preparation of Compound

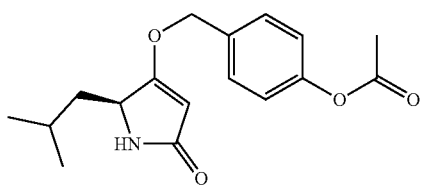 [SMILES: CC(=O)Oc1ccc(COC2=CC(=O)N[C@H]2CC(C)C)cc1]

60121

28.1 Preparation of

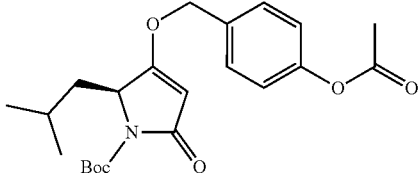 [SMILES: CC(=O)Oc1ccc(COC2=CC(=O)N(C(=O)OC(C)(C)C)[C@H]2CC(C)C)cc1]

60081, Intermediate 42

Intermediate 6 (1.0 g, 3.92 mmol) was dissolved into 20 mL of acetonitrile. K₂CO₃ (595 mg, 4.31 mmol) and 4-acetoxybenzyl bromide (988 mg, 4.31 mmol) were added in turn at room temperature, followed by reflux reaction for 5 hours. After cooling to room temperature, solids were removed by filtration, and the filtrate was dried by evaporation and went through column chromatography for purification to obtain intermediate 42, as a colorless oily substance (406 mg, yield: 26%). Molecular weight: 403.48. $^1$H NMR (400 MHz, CDCl₃) δ 7.35 (d, J=8.5 Hz, 2H), 7.12 (d, J=8.5 Hz, 2H), 5.12 (s, 1H), 4.95 (m, 2H), 4.49 (dd, J=6.8, 3.0 Hz, 1H), 2.30 (s, 3H), 1.80 (m, 3H), 1.53 (s, 9H), 0.89 (d, J=6.3 Hz, 6H). $^{13}$C NMR (100 MHz, CDCl₃) δ 177.19, 169.42, 169.37, 151.05, 149.30, 131.89, 129.13, 122.15, 95.16, 82.65, 72.81, 59.30, 39.48, 28.27, 24.07, 23.83, 23.10, 21.23.

28.2 Preparation of Compound

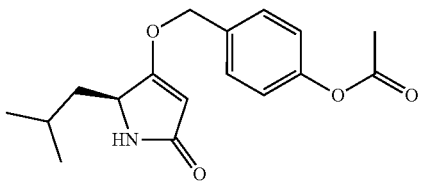 [SMILES: CC(=O)Oc1ccc(COC2=CC(=O)N[C@H]2CC(C)C)cc1]

60121

Intermediate 42 (406 mg, 1.01 mmol) was used as raw material, and the same synthesis method as in Example 1 was adopted to prepare 164 mg of the white solid of Example 28 with a yield of 54%. Molecular weight: 303.6. $^1$H NMR (400 MHz, CDCl₃) δ 7.37 (d, J=8.3 Hz, 2H), 7.11 (d, J=8.3 Hz, 2H), 6.74 (s, 1H), 5.06 (s, 1H), 4.94 (m, 2H), 4.10 (dd, J=9.9, 3.5 Hz, 2H), 2.30 (s, 3H), 1.78 (m, 1H), 1.65 (m, 1H), 1.39 (m, 1H), 0.95 (d, J=6.4 Hz, 6H). $^{13}$C NMR (100 MHz, CDCl₃) δ 177.61, 174.47, 169.42, 150.95, 132.51, 129.12, 122.04, 94.39, 72.52, 56.41, 41.57, 25.58, 23.65, 21.87, 21.22.

Example 29 Preparation of Compound of

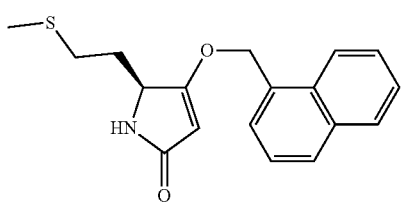 [SMILES: CSCC[C@@H]1NC(=O)C=C1OCc1cccc2ccccc12]

60251

29.1 Preparation of

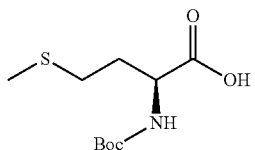 [SMILES: CSCC[C@H](NC(=O)OC(C)(C)C)C(=O)O]

Intermediate 7

The same synthesis method as for intermediate 1 was adopted, and L-methionine was used as raw material, the yield being 99%. A next step reaction could be carried out without further purifying the product.

29.2 Preparation of

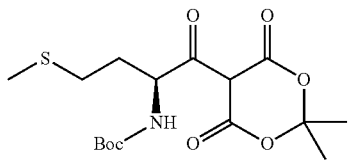

Intermediate 8

The same synthesis method as for intermediate 2 was adopted, the yield being 80%. A next step reaction could be carried out without further purifying the product.

29.3 Preparation of

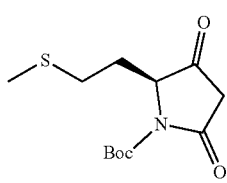 [SMILES: CSCC[C@H]1C(=O)CC(=O)N1C(=O)OC(C)(C)C]

Intermediate 9

The same synthesis method as for intermediate 3 was adopted, and the crude product went through column chromatography for separation and purification to obtain the target product, with a yield of 86%.

29.4 Preparation of

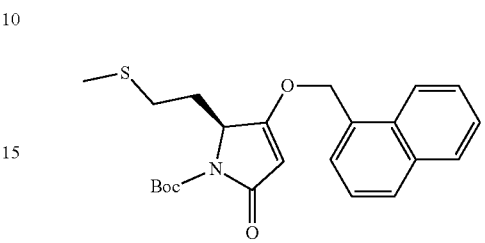

60191, Intermediate 43

Intermediate 9 (1.16 g, 4.24 mmol) was dissolved into 20 mL of acetonitrile. $K_2CO_3$ (645 mg, 4.67 mmol) and 1-bromomethyl naphthalene (1.03 mg, 4.67 mmol) were added in turn at room temperature, followed by reflux reaction for 5 hours. After cooling to room temperature, solids were removed by filtration, and the filtrate was dried by evaporation and went through column chromatography for purification to obtain intermediate 43, as a colorless oily substance (469 mg, yield: 27%). Molecular weight: 413.53. $^1$H NMR (400 MHz, CDCl$_3$) δ 7.89 (m, 3H), 7.50 (m, 4H), 5.42 (m, 2H), 5.29 (s, 1H), 4.55 (dd, J=5.4, 2.7 Hz, 1H), 2.29 (m, 2H), 2.13 (m, 2H), 1.91 (s, 3H), 1.51 (s, 9H). $^{13}$C NMR (100 MHz, CDCl$_3$) δ 175.38, 169.09, 149.14, 133.75, 131.36, 130.24, 129.48, 128.92, 127.99, 126.99, 126.29, 125.11, 123.16, 95.70, 82.75, 72.21, 59.30, 29.34, 28.13, 27.29, 15.54.

29.5 Preparation of Compound

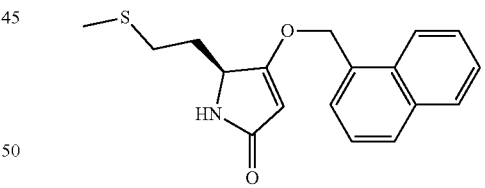

60251

Intermediate 43 (469 mg, 1.13 mmol) was used as raw material, and the same synthesis method as in Example 1 was adopted to prepare 215 mg of the white solid of Example 29 with a yield of 61%. Molecular weight: 313.42. $^1$H NMR (400 MHz, CDCl$_3$) δ 7.91 (m, 3H), 7.52 (m, 4H), 7.05 (s, 1H), 5.40 (m, 2H), 5.26 (s, 1H), 4.22 (dd, J=8.0, 3.8 Hz, 1H), 2.50 (m, 2H), 2.08 (m, 1H), 2.00 (s, 3H), 1.81 (m, 1H). $^{13}$C NMR (100 MHz, CDCl$_3$) δ 176.47, 174.59, 133.85, 131.56, 130.18, 130.07, 128.96, 127.79, 126.92, 126.29, 125.25, 123.40, 94.97, 71.98, 57.15, 31.39, 29.96, 15.50.

Example 30 Preparation of Compound

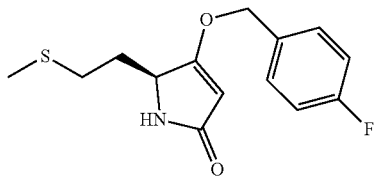 [SMILES: CSCC[C@@H]1NC(=O)C=C1OCc1ccc(F)cc1]

60221

30.1 Preparation of

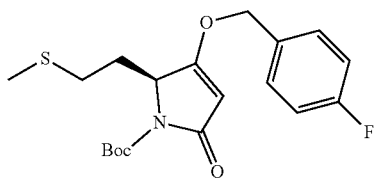 [SMILES: CSCC[C@H]1C(OCc2ccc(F)cc2)=CC(=O)N1C(=O)OC(C)(C)C]

60161, Intermediate 44

Intermediate 9 (920 mg, 3.37 mmol) was dissolved into 15 mL of acetonitrile. K$_2$CO$_3$ (512 mg, 3.71 mmol) and 4-fluorobenzyl bromide (700 mg, 3.70 mmol) were added successively at room temperature, followed by reflux reaction for 5 hours. After cooling to room temperature, solids were removed by filtration, and the filtrate was dried by evaporation and went through column chromatography for purification to obtain intermediate 44, as a colorless oily substance (307 mg, yield: 24%). Molecular weight: 381.46. $^1$H NMR (400 MHz, CDCl$_3$) δ 7.32 (m, 2H), 7.07 (m, 2H), 5.13 (s, 1H), 4.97 (m, 2H), 4.56 (dd, J=5.4, 2.9 Hz, 1H), 2.27 (m, 4H), 2.02 (s, 3H), 1.51 (s, 9H). $^{13}$C NMR (100 MHz, CDCl$_3$) δ 175.38, 168.99, 163.05 (d, J=248.3 Hz), 149.24, 130.06 (d, J=8.6 Hz), 130.04 (d, J=3.2 Hz), 115.93 (d, J=21.8 Hz), 95.78, 82.91, 72.88, 59.28, 29.37, 28.20, 27.51, 15.74. $^{19}$F NMR (376 MHz, CDCl$_3$) δ −112.10.

30.2 Preparation of Compound

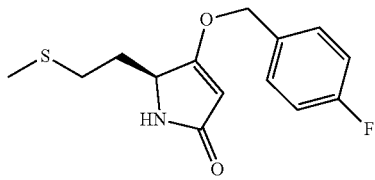 [SMILES: CSCC[C@@H]1NC(=O)C=C1OCc1ccc(F)cc1]

60221

Intermediate 44 (307 mg, 0.80 mmol) was used as raw material, and the same synthesis method as in Example 1 was adopted to prepare 138 mg of the white solid of Example 30 with a yield of 61%. Molecular weight: 281.35. $^1$H NMR (400 MHz, CDCl$_3$) δ 7.33 (dd, J=8.3, 5.2 Hz, 2H), 7.07 (t, J=8.5 Hz, 2H), 5.08 (s, 1H), 4.94 (m, 2H), 4.21 (dd, J=8.0, 3.8 Hz, 1H), 2.54 (m, 2H), 2.12 (m, 1H), 2.07 (s, 3H), 1.81 (m, 1H). $^{13}$C NMR (100 MHz, CDCl$_3$) δ 176.34, 174.48, 162.99 (d, J=247.7 Hz), 130.64 (d, J=3.3 Hz), 129.95 (d, J=8.4 Hz), 115.87 (d, J=21.7 Hz), 95.04, 72.61, 57.06, 31.45, 30.10, 15.61. $^{19}$F NMR (376 MHz, CDCl$_3$) δ −112.64.

Example 31 Preparation of Compound

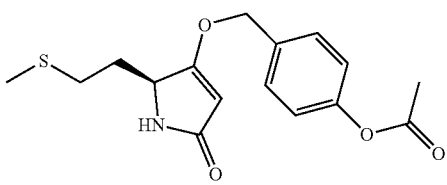 [SMILES: CSCC[C@@H]1NC(=O)C=C1OCc1ccc(OC(C)=O)cc1]

60131

31.1 Preparation of

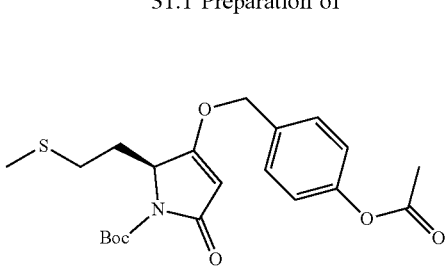

60091, Intermediate 45

Intermediate 9 (400 mg, 1.47 mmol) was dissolved into 5 mL of acetonitrile. K$_2$CO$_3$ (223 mg, 1.62 mmol) and 4-acetoxybenzyl bromide (369 mg, 1.62 mmol) were added successively at room temperature, followed by reflux reaction for 5 hours. After cooling to room temperature, solids were removed by filtration, and the filtrate was dried by evaporation and went through column chromatography for purification to obtain intermediate 45, as a colorless oily substance (160 mg, yield: 26%). Molecular weight: 421.5. $^1$H NMR (400 MHz, CDCl$_3$) δ 7.35 (d, J=8.5 Hz, 2H), 7.11 (d, J=8.5 Hz, 2H), 5.14 (s, 1H), 4.98 (m, 2H), 4.57 (dd, J=5.3, 2.9 Hz, 1H), 2.37 (m, 2H), 2.29 (s, 3H), 2.25 (m, 1H), 2.16 (m, 1H), 2.02 (s, 3H), 1.52 (s, 9H). $^{13}$C NMR (100 MHz, CDCl$_3$) δ 175.42, 169.33, 169.09, 151.11, 149.23, 131.68, 129.25, 122.15, 95.79, 82.92, 72.94, 59.29, 29.33, 28.21, 27.48, 21.19, 15.76.

31.2 Preparation of Compound

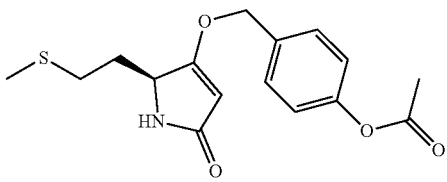 [SMILES: CSCC[C@@H]1NC(=O)C=C1OCc1ccc(OC(C)=O)cc1]

60131

Intermediate 45 (160 mg, 0.38 mmol) was used as raw material, and the same synthesis method as in Example 1 was adopted to prepare 68 mg of the white solid of Example 31 with a yield of 56%. Molecular weight: 321.39. $^1$H NMR (400 MHz, CDCl$_3$) δ 7.37 (d, J=8.2 Hz, 2H), 7.12 (d, J=8.4 Hz, 2H), 6.77 (s, 1H), 5.09 (s, 1H), 4.96 (m, 2H), 4.21 (dd, J=8.1, 3.7 Hz, 1H), 2.55 (m, 2H), 2.30 (s, 3H), 2.12 (m, 1H), 2.08 (s, 3H), 1.82 (m, 1H). $^{13}$C NMR (100 MHz, CDCl$_3$) δ 176.36, 174.33, 169.40, 151.02, 132.35, 129.17, 122.09, 95.02, 72.67, 57.04, 31.40, 30.15, 21.23, 15.60.

Examples of Bioactivity Determination

The activity of the compound of the present invention was determined by a method known in the field. A positive control used was memantine hydrochloride (purchased from Sigma, goods No. M9292) approved by FDA for the treatment of Alzheimer's disease. Other compounds used were prepared according to the methods disclosed in the above examples.

Example 32 Activity Determination in *Drosophila*

*Drosophila* has a classical learning and memory paradigm, known as Pavlov's olfactory-related instantaneous memory. During the training program, a group of about 100 drosophilae were exposed sequentially to two odors, i.e., 3-octanol and 4-methylcyclohexanol, each odor for 60 seconds, and to fresh air for 45 seconds therebetween. During exposure to the first odor, the drosophilae were electrocuted on their feet (1.5-second pulses at 3.5-second intervals, 60V), while no electrocution was exerted during exposure to the second odor. In order to detect "instantaneous memory" (also known as "learning"), drosophilae were transferred to the selection area in the T maze immediately after training and forced to choose between the two odors. The drosophilae in each T-maze arm were then captured, anesthetized, and counted. The behavior index was calculated from the distribution of drosophilae in the T maze. The 50:50 distribution showed that the *Drosophila* didn't learn (PI=0), while the 0:100 distribution indicated that the drosophilae had "perfect learning" (PI=100). In each experiment, the age of the control group was matched with that of the experimental group.

Pharmacodynamic evaluation of the candidate compounds: Drosophilae containing and expressing human Abeta42 gene were selected as a diseased control, and drosophilae containing but not expressing human Abeta42 gene were selected as a healthy control. The day after emergence of the drosophilae, male drosophilae were selected and fed. Starting from the third day, drosophilae were fed with a test medicament (100 μM, 50 μL per 100 drosophilae) for 7 consecutive days, 4 hours each day. The above memory test was performed on the drosophilae on the tenth day.

FIG. 1 shows the effect of compounds 51311, 50561, 51351, 51151, 51121, 51332, 51081, 51091, 51221, 51101, 51071, 51131, 51321, 51341, 51111, and 51301 on memory improvement of drosophilae with Alzheimer's disease. The error line in the figure shows a standard error, *, P<0.001; , P<0.01, *, P<0.05; n.s, with no statistically significant difference.

It can be seen from FIG. 1 that compounds 51311, 50561, 51351, 51151, and 51121 have the best ability to improve the learning and memory of drosophilae.

Figure 2:
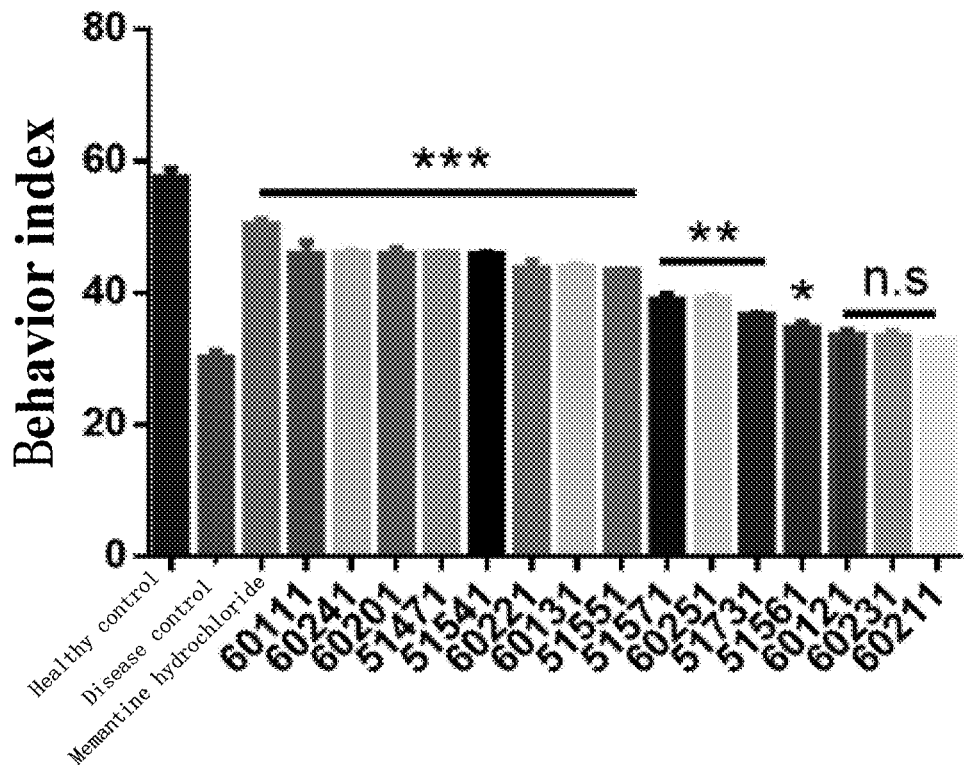
FIG. 2 shows the effect of compounds 60111, 60241, 60201, 51471, 51541, 60221, 60131, 51551, 51571, 60251, 51731, 51561, 60121, 60231, and 60211 on memory improvement of Drosophilae with Alzheimer's disease.

FIG. 2 shows the effect of compounds 60111, 60241, 60201, 51471, 51541, 60221, 60131, 51551, 51571, 60251, 51731, 51561, 60121, 60231, and 60211 on memory improvement of drosophilae with Alzheimer's disease. The error line in the figure shows a standard error, *, P<0.001; , P<0.01, *, P<0.05; n.s, with no statistically significant difference.

It can be seen from FIG. 2 that compound 60111 has quite a good ability to improve learning and memory of drosophilae.

Figure 3:
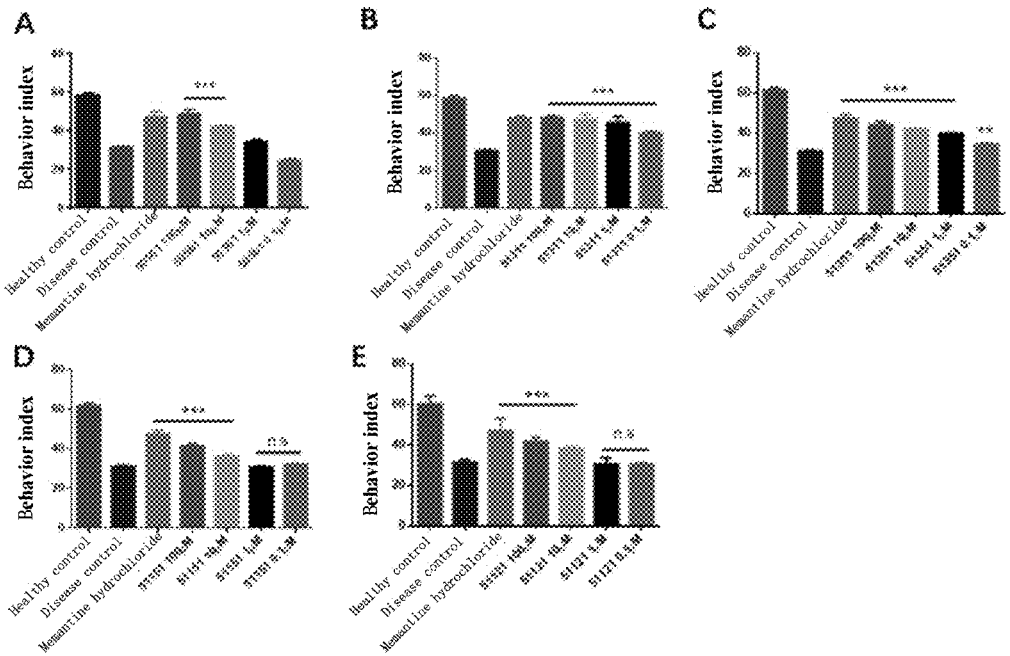
FIG. 3 shows dose-effect relationship of compounds 50561, 51311, 51351, 51151, and 51121 to improve memory of Drosophilae with Alzheimer's disease.

FIG. 3 shows dose-effect relationships of compounds 50561, 51311, 51351, 51151, and 51121 to improve memory of drosophilae with Alzheimer's disease.

It can be seen from FIG. 3 that the activity of each of these five compounds (50561, 51311, 51351, 51151, and 51121) increases to a certain extent with the increase of the dosage thereof, and eventually reaches or exceeds the level of the activity of the positive compound memantine hydrochloride.

Example 33 Activity Determination in Mice

The activity in mice was determined with compound 50561 as an example.

Mice Strain

Transgenic mice containing APP/PS1 were purchased from the Jackson Laboratory of the USA. The transgenic mice were crossbred with B6/C3 background mice. Their offspring were self-bred, genotyped, and each fed in a separate cage for about 8 months. One week before the test, a prescribed dose of medicament was administered to the mice by gavage each day, and then the spatial memory of the mice was measured by water maze test. A water tank with a diameter of 1.5 meters was filled with water at a constant temperature of 25 degrees, and skim milk was added to render the water surface opaque. A transparent platform was placed in a specific quadrant of the water tank. Distant hints were provided as spatial reference. The mice were put into the water and allowed to swim until they found the platform under the surface of water. The whole process was tracked by software, and the time from launching to finding the platform, called a latent period, was recorded thereby. If a mouse could not find the platform within 60 seconds, it was manually guided to the platform and its latent period was recorded as 60 seconds. Four rounds of the above tests were carried out on each mouse every day, with a one-hour interval between every two rounds of tests for the mice to rest. The latent period of each mouse on a day was the average of the four rounds of tests on the same day.

Figure 4:
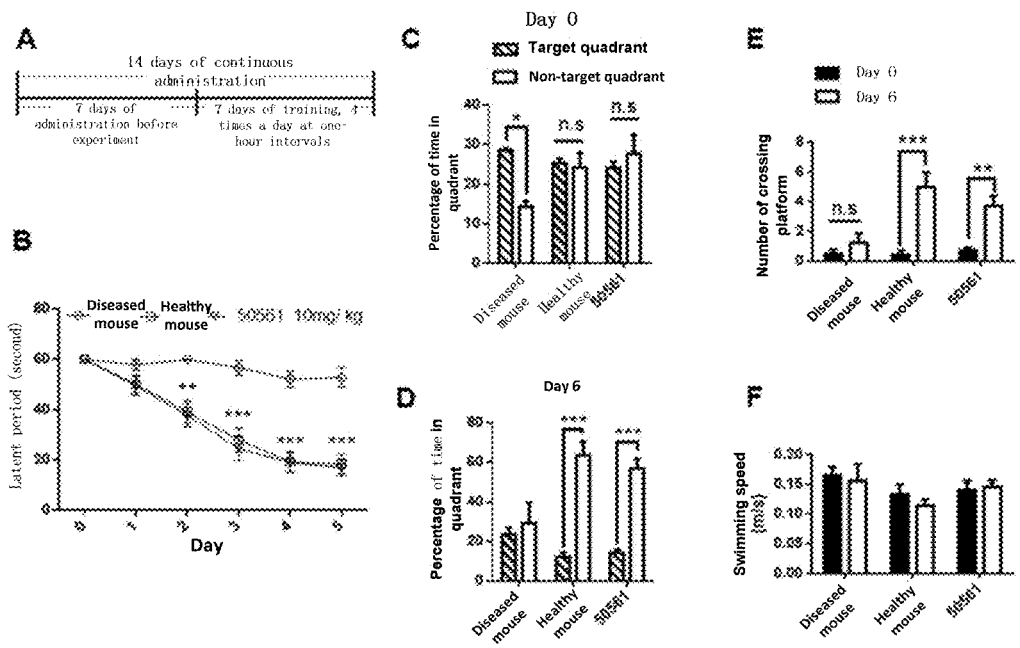
FIG. 4 shows that compound 50561 (10 mg/kg) improves spatial learning and memory of AD mice.

FIG. 4 shows that compound 50561 (10 mg/kg) improved spatial learning and memory of AD mice. A schematically shows administration operations on the mice; B shows latent periods of mice in the water maze tests; C-D show the percentages of residence time of the mice in the target quadrant before and after training; E shows numbers of crossing the platform of the mice before and after training; F shows changes in swimming speed of the mice before and after training. The error line in the figure is a standard error, *, P<0.001; , P<0.01, *, P<0.05; n.s., no statistically significant difference.

It can be seen from FIG. 4 that at the dose of 10 mg/kg, compound 50561 has a good ability to rescue the spatial memory of mice.

Figure 5:
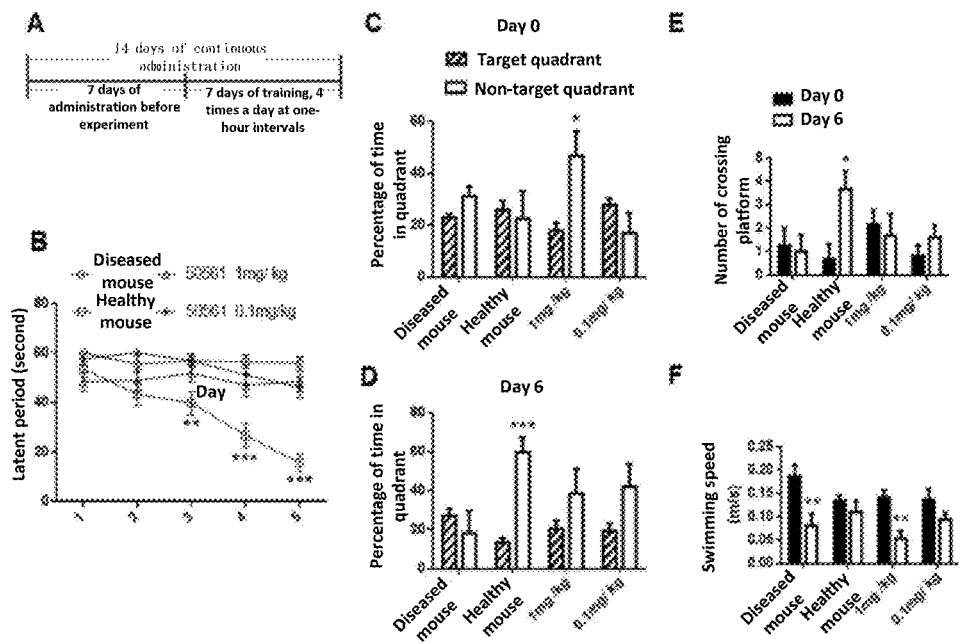
FIG. 5 shows that compound 50561 (1, 0.1 mg/kg) does not improve spatial learning and memory of AD mice, wherein A schematically shows mice administration operations; B shows latent periods in mice water maze tests; C-D show percentages of residence time in a target quadrant of mice before and after training; E shows numbers of crossing a platform by mice before and after training; and F shows changes in swimming speed of mice before and after training.

FIG. 5 shows that compound 50561 (1, 0.1 mg/kg) does not improve spatial learning and memory in AD mice. A schematically shows administration operations on the mice; B shows latent periods of mice in the water maze tests; C-D show the percentages of residence time of the mice in the target quadrant before and after training; E shows numbers of crossing the platform of the mice before and after training; F shows changes in swimming speed of the mice before and after training.

It can be seen from FIG. 5 that compound 50561 has no ability to rescue the spatial memory of mice at a dose of 1 mg/kg or 0.1 mg/kg.

Example 34

Safety was evaluated with compound 50561 as an example.

Safety Evaluation 1 of Compound 50561: Potassium Channel Blockade

Rapidly activated human delayed rectifier outward potassium current (IKr) is mainly mediated by hERG ion channels, and participates in human cardiomyocyte repolarization. Pharmaceutical blockade of this current is the main cause of prolonged QT syndrome, even acute arrhythmia and sudden death clinically.

In this experiment, a stable cell line HEK-hERG (from the Academy of Military Medical Sciences) was selected, and the whole-cell patch clamp technique was used to record the hERG current. Cell suspension was collected and added to a 35 mm culture dish, which was placed on an inverted microscope carrier. After cell attachment, perfusion was performed with an extracellular fluid at a flow rate of 1-2 mL/min. A glass microelectrode was drawn in two steps by a micropipette puller, and after filling with electrode inner fluid, the water resistance of the glass microelectrode was 2-5 MΩ. After the whole cell recording mode was established, the clamping potential was maintained to −80 mV. A depolarization voltage was exerted to +60 mV for 850 ms, followed by repolarization to −50 mV for 1275 ms to induce an hERG tail current. After current stabilization, continuous extracellular perfusion administration from a low concentration to a high concentration was adopted. Starting from the low concentration, continuous perfusion was performed until the efficacy was stable, followed by perfusion of the next concentration. When the inhibitory rate of a compound or positive control to the hERG current was less than 50%, the CV of each of five consecutive current values was less than 10%. When the inhibitory rate of a compound or positive control to the hERG current was more than 50% but less than 70%, the CV of each of five consecutive current values was less than 20%. If a current amplitude was reduced by less than 200 pA, or if the inhibitory rate was more than 70%, the CV of each of five consecutive current values was less than 30%.

A certain amount of a test sample was weighed and dissolved into DMSO to prepare a 30 mM stock solution. Prior to the experiment, the above stock solution was diluted by DMSO 10 times and 3 times step by step, and then the solution was diluted by extracellular fluid to a required concentration. The solution at working concentration should be checked for precipitation before use. If precipitation existed, the stock solution would be diluted to increase the final concentration of DMSO in the extracellular fluid. However, the final concentration of DMSO in the extracellular fluid would not exceed 0.5%. Continuous perfusion from low to high concentrations was done during the experiment. The half inhibitory concentration (IC50) of the test sample was obtained by the best fitting of Logistic equation. The blocking effect of the test sample on hERG is shown in Table 1.

When data were processed, stimulus release and signal acquisition were carried out by the software patchmaster; and a patch clamp amplifier amplified the signal and filtered it to 10 KHz. Fitmaster, excel, spass 21.0, and the like were used for further data analysis and curve fitting. The data were shown as mean values±standard deviation. In data processing, when the blocking effect on hERG was determined, the peak value of a tail current and its baseline were corrected. The inhibitory rates of the tail current were used to show the effects of various compounds at different concentrations. The inhibitory rate=100× (the peak value of the tail current before administration− the peak value of the tail current after administration)/the peak value of the tail current before administration %. IC50 values were fitted by the Hill equation:

$$y = \left[ \frac{max - min}{1 + \left(\frac{[drug]}{IC_{50}}\right)^{n_H}} \right] + min$$

wherein, y: $I/I_{control}$; max: 100%; min: 0%; [drug]: concentration of the test sample; $n_H$: Hill slope; $IC_{50}$: maximum half inhibition concentration of the test substance.

TABLE 1

Blocking Effect of Compound 50561 on hERG

| Con-centration (M) | Inhibitory effect: cell 1 (%) | Inhibitory effect: cell 2 (%) | Inhibitory effect: cell 3 (%)* | Inhibitory effect cell 4 (%) | Mean value ± standard deviation (%) |
|---|---|---|---|---|---|
| 3.00E−07 | −3.08 | 2.01 | −2.32 | 6.75 | 0.84 ± 3.93 |
| 1.00E−06 | −1.69 | 4.62 | 0.78 | 10.02 | 3.43 ± 4.42 |
| 3.00E−06 | 7.24 | 12.91 | 7.90 | 17.32 | 11.34 ± 4.09 |
| 1.00E−05 | 24.13 | 25.26 | 27.76 | 25.53 | 25.67 ± 1.31 |
| 3.00E−05 | 59.63 | 52.91 | 52.24 | 50.18 | 53.56 ± 3.60 |

Figure 6:
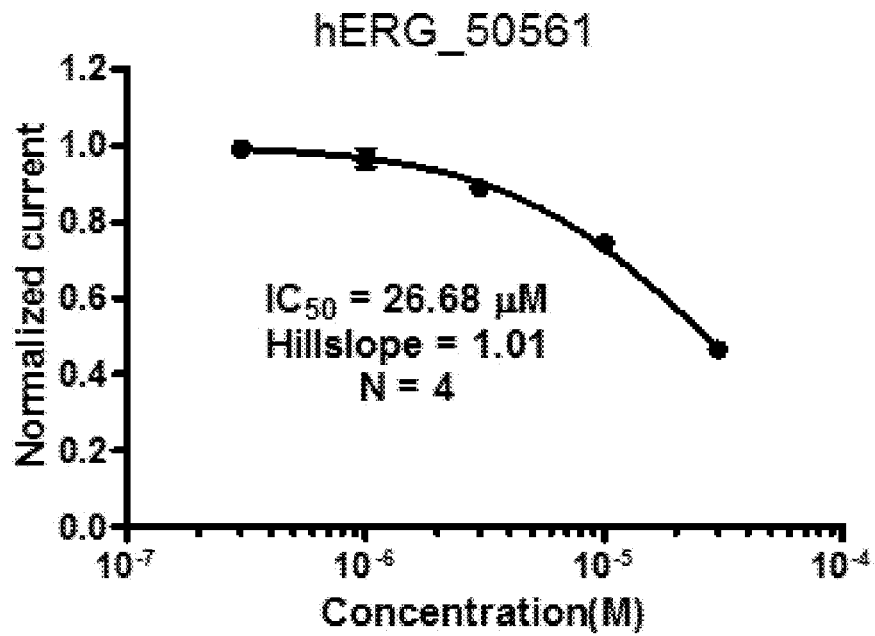
FIG. 6 shows a concentration-effect curve of compound 50561 to hERG potassium channels recorded on an hEGR stable cell line of HEK-293 using the patch clamp technique.

Table 1.
*When cell 3 was provided with 10M treatment, the numerical indicator of leak currents was more than 200 pA, and thus cell 4 was supplemented. It was also included in the final analysis due to the matched effect thereof FIG. 6 is a concentration-effect curve of compound 50561 against hERG potassium channels recorded on an hERG stable cell line of HEK-293 by the patch clamp technique.

To induce a peak current of hERG tail current, the clamping potential was maintained at −80 mV, depolarized to 60 mV for 0.85 s, and then repolarized to −50 mV for 1.275 s. According to the Hill equation, the hERG current inhibitory rate and its corresponding concentration were curve fitted. Each point in the graph was represented by mean value± standard deviation (N=4). Data fitting analysis indicated that the $IC_{50}$ value of compound 50561 against the hERG current was 26.68 M, and the Hill coefficient was 1.01.

Example 35

The safety was evaluated taking compound 50561 as an example.

Safety Evaluation 2 of Compound 50561: Mini Ames Experiment

Histidine auxotrophic strains of *Salmonella typhimurium* were cultured in a special medium with quite a low content of histidine. The strains were difficult to divide due to lack of nutrition. If a test compound has mutagenicity, a large number of cells will undergo reverse mutation, synthesizing histidine by themselves and developing into colonies visible to the naked eye. In view of the close relationship between mutagenicity and carcinogenesis of chemicals, this method has been widely used in screening carcinogens. Some chemicals need metabolic activation to induce mutagenicity. Mammalian microsomal enzyme S9 can be added into the test system to eliminate the influence of metabolic activation on generation of mutagenicity.

After test, in two strains of TA98/100, regardless of the presence or absence of S9, compound 50561 did not cause more than twice of a change in the number of colonies. It was thus considered that it had no obvious mutagenicity. Mice Mini Ames test with compound 50561

TABLE 2

In the absence of S9, compound 50561 does not cause mutation
Without Metabolic Activation

| Strain | Test/Control Article | Dose Level Per Well | Mean Revertants Per Well | Standard Deviation | Ratio Treated/Solvent | Individual Revertant Colony Counts [Background Lawn] |
|---|---|---|---|---|---|---|
| TA98 | DMSO | 0.02 ml | 6.83 | 3.60 | — | 5 [1], 11 [1], 7 [1], 10 [1], 1 [1], 7 [1] |
|  | 50561 | 1.5 µg | 9.00 | 2.65 | 1.32 | 10 [1], 11 [1], 6 [1] |
|  |  | 4 µg | 8.00 | 2.65 | 1.17 | 7 [1], 11 [1], 6 [1] |
|  |  | 10 µg | 8.00 | 3.61 | 1.17 | 5 [1], 7 [1], 12 [1] |
|  |  | 25 µg | 8.33 | 1.53 | 1.22 | 10 [1], 8 [1], 7 [1] |
|  |  | 64 µg | 7.33 | 3.51 | 1.07 | 11 [1], 4 [1], 7 [1] |
|  |  | 160 µg | 7.33 | 3.51 | 1.07 | 7 [3], 4 [3], 11 [3] |
|  |  | 400 µg | 0.00 | 0.00 | 0.00 | 0 [7], 0 [7], 0 [7] |
|  |  | 1000 µg | 0.00 | 0.00 | 0.00 | 0[5 SP], 0 [5 SP], 0 [5 SP] |
|  | 2-NF | 2.0 µg | 421.00 | 37.04 | 61.61 | 407 [1], 393 [1], 463 [1] |
| TA100 | DMSO | 0.02 ml | 24.67 | 3.50 | — | 21 [1], 31 [1], 24 [1], 26 [1], 23 [1], 23 [1] |
|  | 50561 | 1.5 µg | 25.67 | 1.53 | 1.04 | 24 [1], 27 [1], 26 [1] |
|  |  | 4 µg | 25.33 | 1.15 | 1.03 | 24 [1], 26 [1], 26 [1] |
|  |  | 10 µg | 28.67 | 3.51 | 1.16 | 25 [1], 32 [1], 29 [1] |
|  |  | 25 µg | 19.00 | 5.57 | 0.77 | 20 [1], 24 [1], 13 [1] |
|  |  | 64 µg | 23.33 | 4.62 | 0.95 | 26 [1], 26 [1], 18 [1] |
|  |  | 160 µg | 17.33 | 2.08 | 0.70 | 15 [4], 19 [4], 18 [4] |
|  |  | 400 µg | 0.00 | 0.00 | 0.00 | 0 [7], 0 [7], 0 [7] |
|  |  | 1000 µg | 0.00 | 0.00 | 0.00 | 0 [5 SP], 0 [5 SP], 0 [5 SP] |
|  | SA | 0.2 µg | 195.33 | 16.50 | 7.92 | 179 [1], 212 [1], 195 [1] |

TABLE 3

In the absence of S9, compound 50561 does not cause mutation
With Metabolic Activation

| Strain | Test/Control Article | Dose Level Per Well | Mean Revertants Per Well | Standard Deviation | Ratio Treated/Solvent | Individual Revertant Colony Counts [Background Lawn] |
|---|---|---|---|---|---|---|
| TA98 | DMSO | 0.02 ml | 8.33 | 2.16 | — | 11 [1], 7 [1], 11 [1], 8 [1], 7 [1], 6 [1] |
|  | 50561 | 1.5 µg | 8.67 | 3.79 | 1.04 | 6 [1], 13 [1], 7 [1] |
|  |  | 4 µg | 13.33 | 3.51 | 1.60 | 10 [1], 13 [1], 17 [1] |
|  |  | 10 µg | 9.33 | 3.06 | 1.12 | 12 [1], 6 [1], 10 [1] |
|  |  | 25 µg | 12.67 | 7.09 | 1.52 | 19 [1], 14 [1], 5 [1] |
|  |  | 64 µg | 12.33 | 2.52 | 1.48 | 15 [1], 12 [1], 10 [1] |
|  |  | 160 µg | 7.00 | 3.00 | 0.84 | 10 [1], 7 [1], 4 [1] |
|  |  | 400 µg | 0.00 | 0.00 | 0.00 | 0 [7], 0 [7], 0 [7] |
|  |  | 1000 µg | 0.00 | 0.00 | 0.00 | 0[5 SP], 0 [5 SP], 0 [5 SP] |
|  | 2-AA | 0.4 µg | 297.67 | 21.03 | 35.72 | 318 [1], 276 [1], 299 [1] |
| TA100 | DMSO | 0.02 ml | 32.67 | 2.80 | — | 36 [1], 30 [1], 30 [1], 31 [1], 33 [1], 36 [1] |
|  | 50561 | 1.5 µg | 25.33 | 5.69 | 0.78 | 30 [1], 19 [1], 27 [1] |
|  |  | 4 µg | 30.33 | 2.89 | 0.93 | 27 [1], 32 [1], 32 [1] |
|  |  | 10 µg | 32.33 | 4.04 | 0.99 | 37 [1], 30 [1], 30 [1] |
|  |  | 25 µg | 28.67 | 5.69 | 0.88 | 35 [1], 27 [1], 24 [1] |
|  |  | 64 µg | 31.00 | 5.57 | 0.95 | 36 [1], 32 [1], 25 [1] |
|  |  | 160 µg | 28.33 | 2.08 | 0.87 | 26 [3], 29 [3], 30 [3] |
|  |  | 400 µg | 0.00 | 0.00 | 0.00 | 0 [7], 0 [7], 0 [7] |
|  |  | 1000 µg | 0.00 | 0.00 | 0.00 | 0 [5 SP], 0 [5 SP], 0 [5 SP] |
|  | 2-AA | 0.4 µg | 317.67 | 9.07 | 9.72 | 319 [1], 326 [1], 308 [1] |

Example 36

Safety Evaluation 3 of Compound 50561: MTD Experiment

Mice are commonly used rodents to evaluate the toxicity of a test sample and are also an important part of early preclinical safety evaluation. In this experiment, the toxicity of compound 50561 was tested by administering a dose gradient thereof to the mice by gavage and observing its toxicity.

This experiment was designed such that for each dose centration, 10 mice were tested, including half males and half females. The males each weighed about 18-23 grams, and the females each weighed about 17-21 grams. They were randomly grouped by a simple randomization procedure. All the animals used in the experiment weighed between ±20% of the average body weight of their respective genders. If there are not enough animals in the study to meet the weight range required thereby, notify the responsible person of the project to take reasonable measures. Animals must be adapted to the laboratory for at least three days. During this period, daily cage observation was conducted once a day, and a detailed clinical observation was necessary before the experiment. Any animal with symptoms or physical abnormalities would be reported to the attending veterinarian and responsible person of the project, and excluded whenever possible. Animals suitable for experimentation will be assigned to respective experimental groups according to the random grouping method described above.

During the experiment, after administration, all animals were observed continuously for 4 hours; from the end of administration till 3 days thereafter, observations were carried out twice each day, one in the morning and the other in the afternoon; and then observation was carried out once a day. Observations included but were not limited to: skin, hair, eyes, ears, nose, mouth, chest, abdomen, external genitals, limbs, and feet. The respiratory and circulatory systems, autonomic effects (such as salivation), and nervous system (such as tremors, convulsions, stress responses, and abnormal behaviors) should be focused on. Complete anatomical examinations would be performed on all animals that had died, were dying, or planned to be euthanized. Animals found dead outside of fixed working hours could be placed in the refrigerator overnight and dissected immediately on the next working day. At the end of the experiment (14th day after administration), all animals requiring autopsy would be euthanized and autopsied.

External abnormalities in animals, such as palpable masses, should be examined in detail. The skin would be cut along the midline of the abdomen, and any subcutaneous mass would be confirmed in conjunction with the findings in the observations of animal symptoms. The abdominal cavity, thoracic cavity, and cranial cavity were observed for any abnormality. Diseased organs were removed, weighed, recoded, and kept in a fixative fluid.

Results were shown in Table 4. The maximum tolerance of CR mice to compound 50561 was 500 mg/kg>MTD≥250 mg/kg.

TABLE 4

| concentration | Survival number | Remarks |
|---|---|---|
| 250 mg/kg | 10 | Body weight decreased by about 2 g, which was quickly recovered, and the body was in good condition. |
| 500 mg/kg | 8 | Body weight decreased by about 2 g; individual activity decreased; and the body was in good condition. There was no abnormality in the organs of the dead individuals. |
| 750 mg/kg | 0 | No abnormality of organs in dead individuals. |
| 1000 mg/kg | 0 | No abnormality of organs in dead individuals. |

Example 37

Pharmacokinetic evaluation was performed with compound 50561 as an example.

Distribution of a medicament in the body is one of the important indicators to determine the dose and efficacy of the medicament. Thus, excellent candidate compounds should have good pharmacokinetic characteristics. In addition, since the compound of the present invention is intended to be used for the treatment of Alzheimer's disease, which is a disease of the central nervous system, the distribution pattern of the compound in the brain and the blood is also one of the subjects to be investigated. In this experiment, compound 50561 was administered to mice by oral or by gavage, and the concentrations of the compound in blood and brain were measured at specific time points to determine the pharmacokinetic parameters.

Forty-eight male ICR mice purchased from Shanghai Sippr-BK Lab. Animal Co. Ltd were used in this experiment. The oral group was fasted for 10-14 hours before administration, and feeding was restored 4 hours after administration. Samples were collected from the intravenous administration group 0.083 h, 0.25 h, 0.5 h, 1 h, 2 h, 4 h, 8 h, and 24 h after administration, respectively; while for the oral administration group, about 0.5 mL of blood was collected from the heart 0.25 h, 0.5 h, 1 h, 2 h, 4 h, 6 h, 8 h, and 24 h after administration, respectively. Heparin sodium was used for anticoagulation. Blood samples were collected and placed on ice, and plasma was separated by centrifugation (centrifugation conditions: 8000 rpm, 6 minutes, 4C). The collected plasma was stored at −80° C. before analysis. After collecting plasma samples, brain tissues were collected, washed with normal saline, water-absorbed by filter paper, weighed immediately, and then placed in labeled tubes (one tube for one brain tissue). The samples to be tested were temporarily placed on ice before being stored in a −80° C. refrigerator.

The analysis methods of biological samples and the analysis of all samples were done by Medicilon Pharmaceutical Technology (Shanghai) Co., Ltd. The intraday accuracy evaluation of the quality control samples was carried out while analyzing the samples, and the accuracy of over 66.7% of the quality control samples was required to be between 80-120%.

When calculating the pharmacokinetic parameters, the BLQ before $C_{max}$ (including "No peak") was calculated as 0; BLQ occurring after $C_{max}$ (including "No peak") was not involved in the calculation. WinNonlin Professional V 5.2 (Pharsight, USA) was adopted to calculate the following pharmacokinetic parameters: $AUC_{(0-t)}$, $AUC_{(0-\infty)}$, $T_{1/2}$, $MRT_{(0-\infty)}$, $C_{max}$, and $T_{max}$. The tissue/plasma ratio was to be calculated by the following formula based on the blood concentration data at different time points:

Tissue/plasma ratio (mL/g)=tissue blood concentration/plasma blood concentration.

Figure 7:
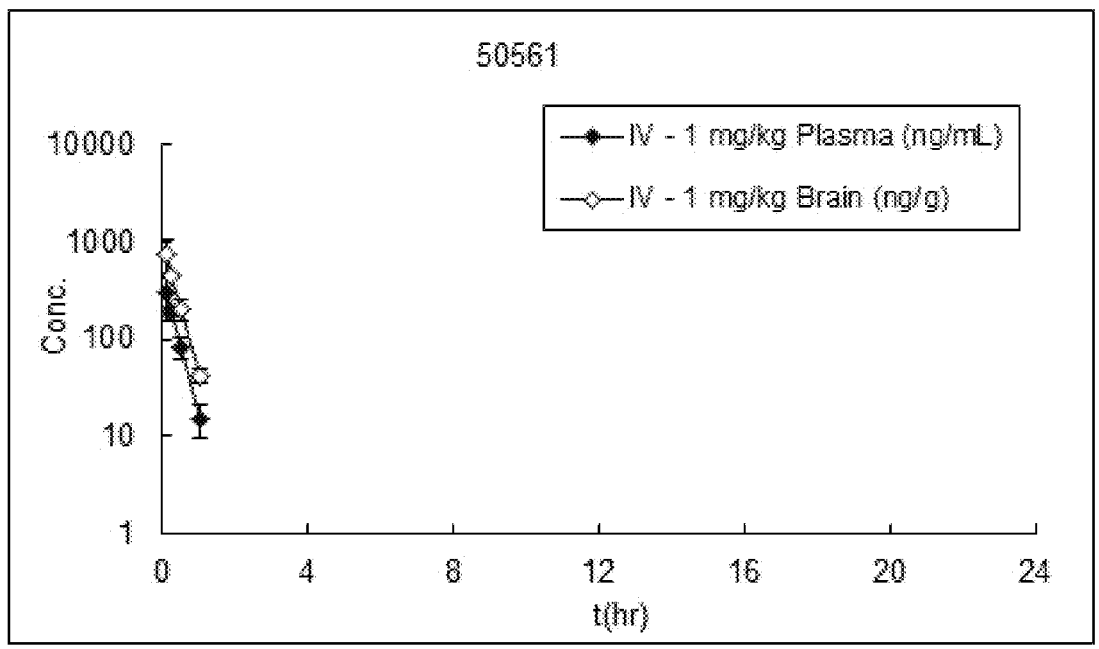
FIG. 7 shows plasma and brain medicament concentration-time curves after intravenous injection of compound 50561.
Figure 8:
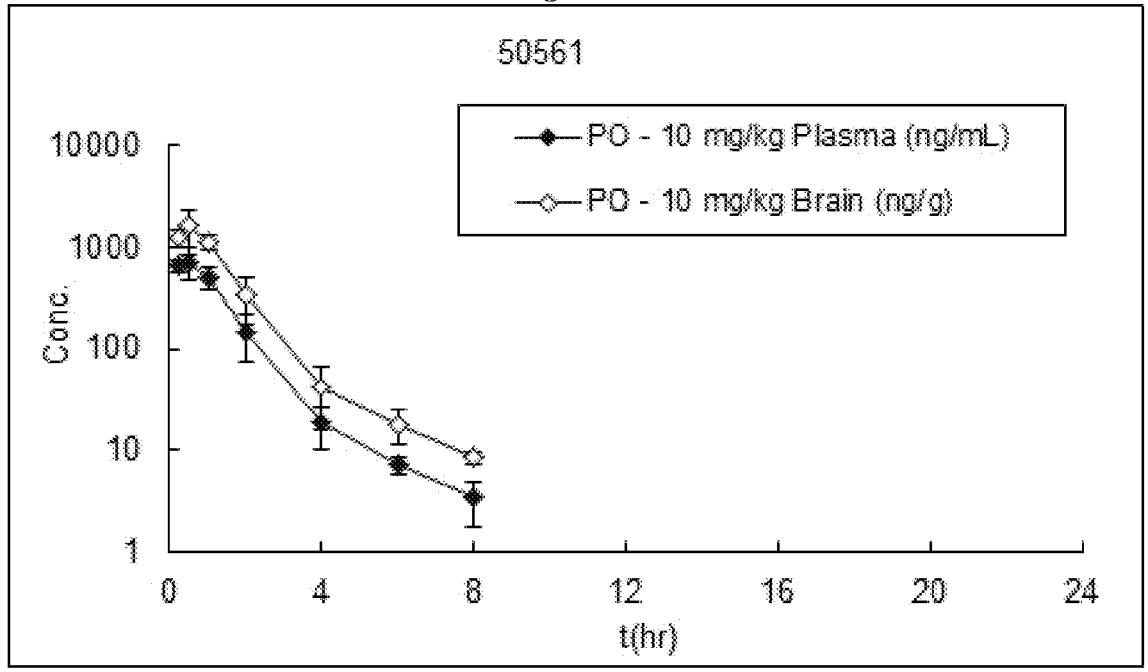
FIG. 8 shows plasma and brain medicament concentration-time curves after oral administration of compound 50561.

FIG. 7 and FIG. 8 show the plasma and brain tissue concentration-time curves in ICR mice after intravenous and oral administration of compound 50561, respectively. The ratios of brain tissue to plasma in the animals were shown in Table 5.

FIG. 7 shows the plasma and brain concentration-time curves after intravenous injection of compound 50561.

FIG. 8 shows the plasma and brain concentration-time curves after oral administration of compound 50561.

TABLE 5

Blood Concentration of ICR Mice afterIntravenous or Oral Administration of Ccompound 50561

50561-IV-1 mg/kg

| Time (hr) | G1-1 | G1-2 | G1-3 | Mean | SD |
|---|---|---|---|---|---|
| Blood concentration (ng/mL) | | | | | |
| 0.083 | 327.86 | 145.16 | 434.45 | 302.49 | 146.30 |
| 0.25 | 188.41 | 180.29 | 215.73 | 194.81 | 18.57 |
| 0.5 | 58.15 | 98.13 | 89.73 | 82.00 | 21.08 |
| 1 | 18.27 | 8.99 | 18.70 | 15.32 | 5.49 |
| 2 | BLQ | BLQ | BLQ | NA | NA |
| 4 | BLQ | BLQ | BLQ | NA | NA |
| 8 | BLQ | BLQ | BLQ | NA | NA |
| 24 | BLQ | BLQ | BLQ | NA | NA |
| Brain tissue concentration (ng/G) | | | | | |
| 0.083 | 853.63 | 383.96 | 977.10 | 738.23 | 312.96 |
| 0.25 | 461.84 | 435.34 | 465.70 | 454.29 | 16.53 |
| 0.5 | 147.71 | 251.60 | 211.84 | 203.72 | 52.42 |
| 1 | 42.57 | 35.43 | 51.45 | 43.15 | 8.02 |
| 2 | BLQ | BLQ | BLQ | NA | NA |
| 4 | BLQ | BLQ | BLQ | NA | NA |
| 8 | BLQ | BLQ | BLQ | NA | NA |
| 24 | BLQ | BLQ | BLQ | NA | NA |
| Brain/plasma ratio (mL/G) | | | | | |
| 0.083 | 2.604 | 2.645 | 2.249 | 2.499 | 0.218 |
| 0.25 | 2.451 | 2.415 | 2.159 | 2.342 | 0.159 |
| 0.5 | 2.540 | 2.564 | 2.361 | 2.488 | 0.111 |
| 1 | 2.330 | 3.941 | 2.751 | 3.007 | 0.835 |
| 2 | NA | NA | NA | NA | NA |
| 4 | NA | NA | NA | NA | NA |
| 8 | NA | NA | NA | NA | NA |
| 24 | NA | NA | NA | NA | NA |

50561-PO-10 mg/kg

| Time (hr) | G2-1 | G2-2 | G2-3 | Mean | SD |
|---|---|---|---|---|---|
| Blood concentration (ng/mL) | | | | | |
| 0.25 | 754.39 | 655.31 | 548.11 | 652.60 | 103.17 |
| 0.5 | 1020.50 | 631.98 | 529.57 | 727.35 | 258.99 |
| 1 | 364.54 | 599.81 | 532.80 | 499.05 | 121.21 |
| 2 | 128.34 | 83.99 | 219.54 | 143.95 | 69.11 |
| 4 | 27.74 | 18.40 | 10.71 | 18.95 | 8.53 |
| 6 | 6.37 | 6.30 | 8.82 | 7.16 | 1.43 |
| 8 | 4.77 | 3.88 | 1.63 | 3.43 | 1.62 |
| 24 | BLQ | BLQ | BLQ | NA | NA |
| Brain tissue concentration (ng/G) | | | | | |
| 0.25 | 1469.79 | 1042.09 | 1147.13 | 1219.67 | 222.89 |
| 0.5 | 2484.73 | 1280.85 | 1048.58 | 1604.72 | 770.91 |
| 1 | 905.85 | 1290.84 | 1149.69 | 1115.46 | 194.76 |
| 2 | 277.53 | 206.08 | 520.70 | 334.77 | 164.94 |
| 4 | 65.84 | 44.67 | 14.52 | 41.68 | 25.9 |
| 6 | 11.72 | 17.40 | 25.83 | 18.32 | 7.10 |
| 8 | 7.52 | 9.49 | BLQ | 8.50 | 1.39 |
| 24 | BLQ | BLQ | BLQ | NA | NA |
| Brain/plasma ratio (mL/G) | | | | | |
| 0.25 | 1.948 | 1.590 | 2.093 | 1.877 | 0.259 |
| 0.5 | 2.435 | 2.027 | 1.980 | 2.147 | 0.250 |
| 1 | 2.485 | 2.152 | 2.158 | 2.265 | 0.191 |
| 2 | 2.163 | 2.454 | 2.372 | 2.329 | 0.150 |
| 4 | 2.373 | 2.428 | 1.355 | 2.052 | 0.604 |
| 6 | 1.839 | 2.764 | 2.929 | 2.511 | 0.587 |
| 8 | 1.575 | 2.443 | NA | 2.009 | 0.614 |
| 24 | NA | NA | NA | NA | NA |

It can be concluded that the content of compound 50561 in brain tissue was higher than that in the blood after intravenous injection and oral administration, which indicated that the compound has good blood-brain barrier permeability.

INDUSTRIAL APPLICABILITY

The present invention provides new compounds, and preparation methods and use thereof. The general structural formula of the compounds is shown in Formula I. Animal experiments show that the compounds of the present invention have the effect of saving the memory of animal models. The compounds are of high safety, have no mutagenicity, can stay in blood for several hours after oral or intravenous injection, and can enter the brain, and thus can be used to prepare a medicament for treating Alzheimer's disease, Parkinson's disease, Huntington's disease, vascular dementia, schizophrenia, and autism among others.

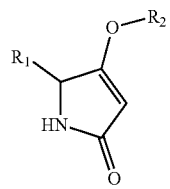

Formula I

The invention claimed is:

1. A compound shown in Formula I or a salt thereof:

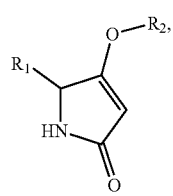

Formula I wherein in Formula I, $R_1$ is selected from

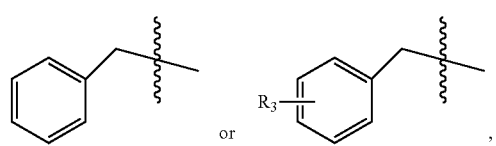

or

R₃ being a $C_1$-$C_6$ alkoxy group; and
R₂ is selected from
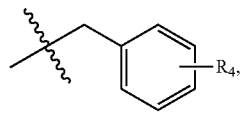
R₄ being a 2-position monosubstituted halogen, a 3-, or 4-position monosubstituted C1-C6 alkyl, an ester group, or a 4-position substituted —CN or a 4-position substituted —$NO_2$;
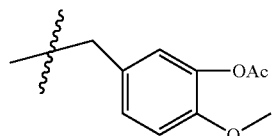 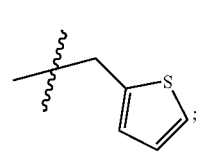
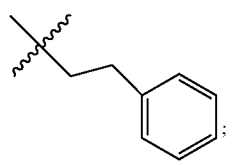
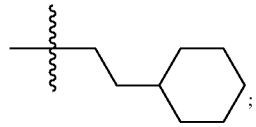
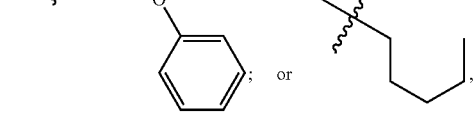
in which ⸘ designates a connecting end.
2. The compound of claim 1, wherein the compound shown in Formula I is one of the following compounds:
51121
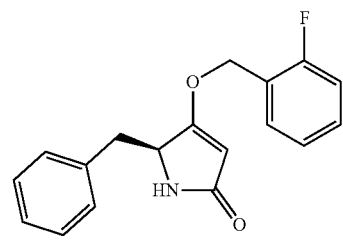
51091
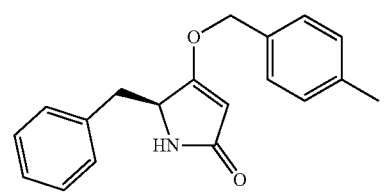
51471
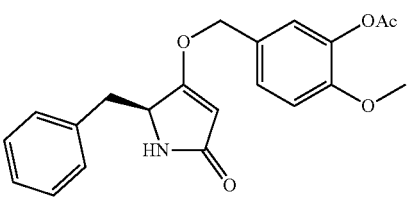
51351
51332
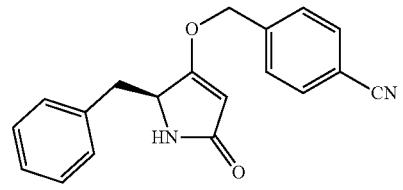
51081
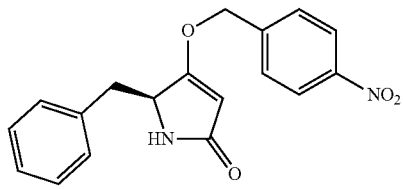
51151
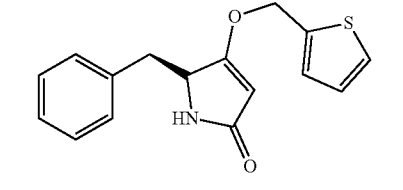
51571
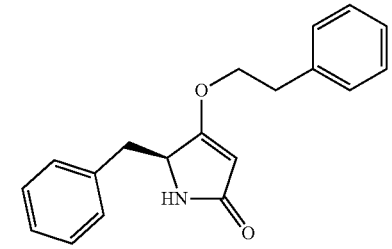
51731
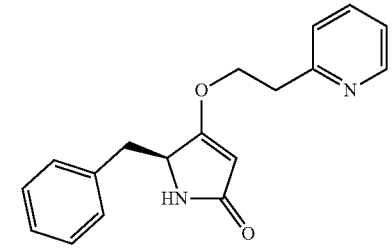

-continued

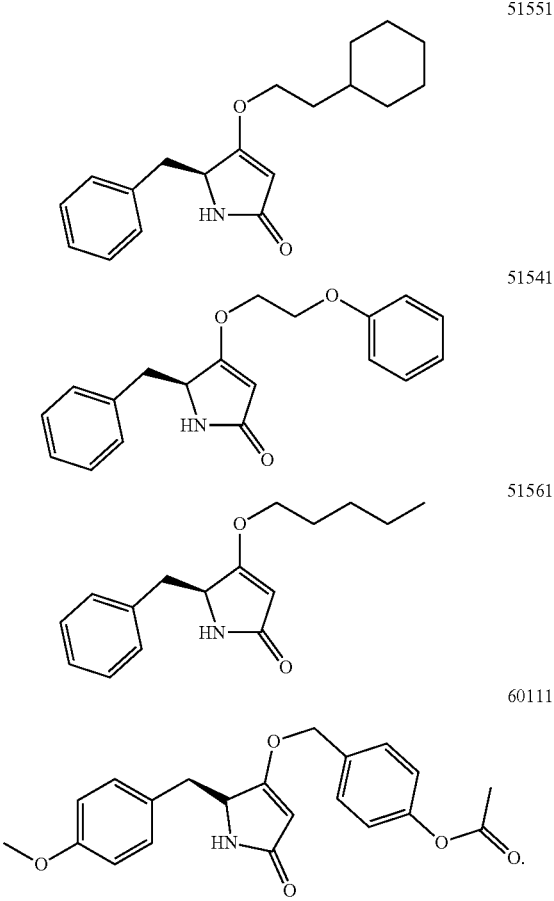

51551

51541

51561

60111

3. A method for preparing the compound of claim 1, comprising the following steps:
   1) reacting a compound shown in Formula II with a compound shown in Formula III to obtain a compound shown in Formula IV, Formula II -continued

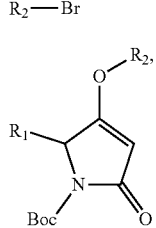

Formula III

Formula IV wherein in above Formula II and Formula IV, $R_1$ has the same definition as in Formula I, and Boc represents tert-butoxycarbonyl group; and
in above Formula III and Formula IV, $R_2$ has the same definition as in Formula I; and
2) removing the compound shown in Formula IV from Boc protection to obtain the compound shown in Formula I of claim 1.

4. The method of claim 3, wherein in step 1),
a molar ratio of the compound shown in Formula II to the compound shown in Formula III is 1:1-10;
the reaction is carried out under an alkaline condition;
the reaction is carried out at a reaction temperature of 0-100° C.;
the reaction is carried out for a reaction time of 0.1-24 hours; and
the reaction is carried out in an organic solvent.

5. The method of claim 3, wherein in step 2),
the removal of Boc protection is carried out under the action of trifluoroacetic acid;
a molar ratio of the compound shown in Formula IV to trifluoroacetic acid is 1:1-20;
a reaction temperature during the removal of Boc protection is −10 to 30° C.;
a reaction time for removal of Boc protection is 0.5-24 hours; and
the removal of Boc protection is carried out in an organic solvent.

6. A compound shown in Formula 50561 or a salt thereof:

50561

* * * * *